(12) United States Patent
Viovy et al.

(10) Patent No.: US 6,830,670 B1
(45) Date of Patent: Dec. 14, 2004

(54) HEAT-SENSITIVE MEDIUM FOR SEPARATING SPECIES IN A SEPARATING CHANNEL AND USE THEREOF

(75) Inventors: Jean-Louis Viovy, Paris (FR); Dominique Hourdet, Bry sur Marne (FR); Jan Sudor, Paris (FR)

(73) Assignees: Institut Curie, Paris Cedex 05 (FR); Centre National de la Recherche Scientifique (C.N.R.S.), Paris (FR); Universite Pierre et Marie Curie-Paris VI, Paris (FR)

( * ) Notice: Subject to any disclaimer, the term of this patent is extended or adjusted under 35 U.S.C. 154(b) by 0 days.

(21) Appl. No.: 09/869,382

(22) PCT Filed: Dec. 28, 1999

(86) PCT No.: PCT/FR99/03304
§ 371 (c)(1),
(2), (4) Date: Oct. 1, 2001

(87) PCT Pub. No.: WO00/40958
PCT Pub. Date: Jul. 13, 2000

(30) Foreign Application Priority Data

Dec. 30, 1998 (FR) .............................................. 98 16676

(51) Int. Cl.[7] ...................... G01N 27/447; G01N 27/453
(52) U.S. Cl. ........................ 204/455; 204/456; 204/469; 204/605
(58) Field of Search ................................ 204/455, 456, 204/469, 601, 605

(56) References Cited

U.S. PATENT DOCUMENTS 5,196,099 A * 3/1993 Mori et al. .................. 204/456
5,238,545 A * 8/1993 Yoshioka et al. ........... 204/462
5,883,211 A * 3/1999 Sassi et al. ............... 526/307.2
5,885,432 A * 3/1999 Hooper et al. .............. 204/469

FOREIGN PATENT DOCUMENTS

EP 0 583 814 2/1994
WO WO 98/10274 3/1998

OTHER PUBLICATIONS

F. L'Alloret et al., "Reversible Thermoassociation of Water–Soluble Polymers", Revue De L'Institut Francais Du Petrole, vol. 52, No. 2, Mar. 1997, pp 117–128.

D. Hourdet et al., "Synthesis of thermoassociative copolymers", POLYMER, vol. 38, No. 10, May 1997, pp 2535–2547.

D. Hourdet, "Thermothickening Polyelectrolytes", Polymer Preprints, vol. 34, No. 1, 1993, pp 972–973.

* cited by examiner

Primary Examiner—Kaj K. Olsen
(74) Attorney, Agent, or Firm—Young & Thompson

(57) ABSTRACT

A medium comprises an electrolyte wherein is dissolved at least an assembly of block copolymers characterized in that the block copolymers: are present in the electrolyte at a concentration level to provide the medium with the property of reversibly passing from a state of viscosity V1, obtained at a temperature T1, to a viscosity state V2 greater by at least 100% than V1, obtained at a temperature T2, and comprise in their structure at least: two non-contiguous polymeric segments having in the electrolyte a lower critical solubility temperature (LCST) and having an average number of atoms along their skeleton more than 50; and a polymeric segment soluble in the electrolyte at temperatures T1 and T2. The invention also concerns the use of the medium for separating analytes.

33 Claims, 12 Drawing Sheets

Figure 1:
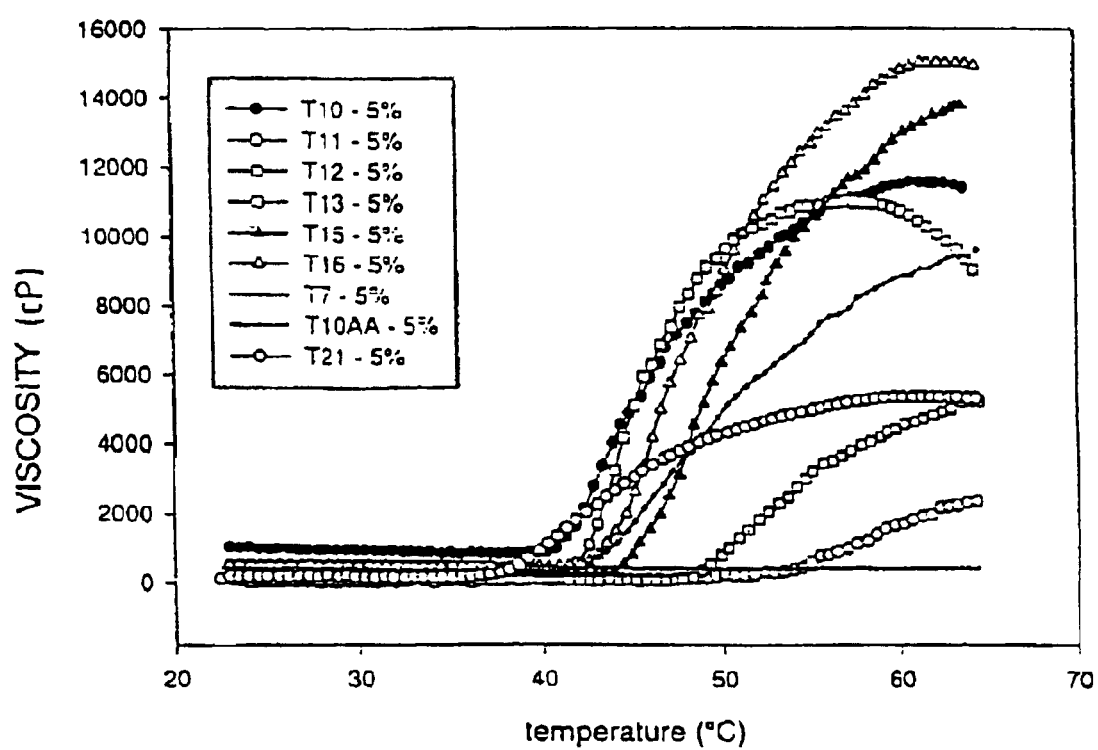

HEAT-SENSITIVE MEDIUM FOR SEPARATING SPECIES IN A SEPARATING CHANNEL AND USE THEREOF

The present invention relates to the field for separating, identifying and/or analyzing particles, molecules or macromolecules, and more particularly nucleic acids, in a channel, for example in a microfluidic system or more particularly in the context of capillary electrophoresis.

BACKGROUND OF THE INVENTION

Gel electrophoresis has numerous applications for separating charged particles, molecules and macromolecules, and in particular biological macromolecules such as nucleic acids (DNA, RNA, oligonucleotides), proteins, polypeptides, glycopeptides and polysaccharides. A particularly important application is sequencing, that is to say the reading of the genetic code of DNA. It is most often carried out in flat and macroscopic gels (having a thickness of the order of 1 to several mm), composed of agarose or polyacrylamide. More recently, other gels derived from acrylamide and a whole series of acrylate or methacrylate gels have been proposed for improving this or that property of the gel. In particular, in patent U.S. Pat. no. 5,164,057, there has been proposed the use of polymers having a lower critical solution temperature (abbreviated hereinafter LCST in the present application) for controlling the hydrophilic/hydrophobic character in a permanently and irreversibly crosslinked gel, used in electrophoresis.

In spite of these improvements, planar gel electrophoresis has many disadvantages.

It requires a relatively substantial amount of manual work for the preparation of the gel, which can only be used once, and for subsequent visualization of the migration distances. Reproducibility of the experiments from one gel to another is difficult to obtain because the properties of the gel depend on the exact preparation conditions. Given the production of heat linked to the current, fairly low low voltages have to be applied, leading to long separation times. Finally, planar electrophoresis is difficult to automate and to quantify. For these different reasons, macroscopic gel electrophoresis tends to be overtaken by techniques in which the separation or more generally the analysis of the constituents of a sample is carried out in channels with a high surface/volume ratio, such as cylindrical capillaries, or channels with a planar submillimetric section which are prepared in a material (which are called "chips", microchannels or microfluidic systems). Examples of such separations are given for example in "Capillary electrophoresis in analytical biotechnology", Righetti ed., CRC press, 1996, or in Cheng, J. et al., (1996), Molecular Diagnosis, 1, 183–200.

In the text which follows, all the methods involving an electrophoretic separation in one channel or several channels of which at least one of the dimensions is of a submillimetric dimension will be designated by the name "capillary electrophoresis" (CE). "Microfluidic system" will designate more generally any system in which the analysis of species is carried out by virtue of the transport of the said species and/or of fluids within a channel or a set of channels of which at least one of the dimensions is submillimetric.

CE and microfluidic systems allow more rapid and higher resolution separations than gels, do not require an anticonvective medium, and their properties have been widely used to carry out separations of ions in a liquid medium.

However, a large proportion of analytes which it is desired to separate by electrophoresis, and in particular those encountered in biology, have, in a homogeneous viscous medium, a mobility which is independent of their size and can only be satisfactorily separated in a medium with obstacles. The gels used in traditional electrophoresis in particular consist of portions of macromolecular chains or of fibres which are connected to each other and cannot be crossed by the analytes. The latter have to create passages along the pores present between the macromolecular segments of the gel, which gives rise to the desired separation. In the first applications of CE to DNA and to proteins, use was often made of permanent gels which are crosslinked inside the capillary. This has many disadvantages: the preparation of a truly homogeneous gel with no bubbles inside a capillary is delicate. The gel becomes degraded relatively rapidly by hydrolysis and is "contaminated" by impurities present in the samples, which eventually damage the performance features of the separation, or even block the capillary after a limited number of separations. Given the production cost and/or the difficulty of manufacturing a capillary filled with gel, this defect makes the cost of this approach prohibitive.

Currently, the great majority of separations of biological macromolecules carried out in CE make use of solutions of entangled linear water-soluble polymers having the advantage of being replaceable as often as necessary. At a fairly high concentration, that is significantly above the entanglement threshold, the various polymers in the solution become entangled and constitute a continuous transient network of topological obstacles which cannot be crossed by the analytes, thus conferring electrophoretic separation properties on the solution.

These water-soluble polymer solutions are satisfactory in some applications, but also have numerous limitations.

The first of these limitations is electroosmosis, a simultaneous movement of the separation medium due to the presence of charges on the walls of the capillary or of the channel. As this movement is often variable over time and nonuniform, it hampers the reproducibility of the measurements and the resolution. Numerous methods have been proposed for combating it, such as treating the surface of the capillaries by adsorption of essentially neutral species on the walls of the separating channel prior to the actual separation (Wiktorowicz et al., Electrophoresis, 11, 769, 1990, Tsuji et al., J. Chromatogr. 594, 317 (1992), or by treating the capillary with an acidic solution (Fung et al., Anal. Chem. 67, 1913, (1995)). These methods have the advantage of being inexpensive and of being capable of being repeated several times in order to regenerate a capillary, but often only partially reduce the electroosmosis. Methods for the irreversible grafting of an essentially neutral polymeric layer on the walls have also been proposed, as for example described in U.S. Pat. No. 4,680,201. Ready-to-use treated capillaries are thus commercially available. These irreversibly treated capillaries lead to a good reduction of electroosmosis for a certain number of separations, but their shelf life is limited and their cost is high.

Another major disadvantage of electrokinetic separations in polymer solutions is that the resolution and the separable range of sizes are better with solutions which are relatively concentrated and of high molecular masses (Mitnik et al., J. Chrom. A, 710, 309 (1995); Goetzinger et al., Electrophoresis, 19, 242, 1998)). This is attributed to deformations of the separating matrix which limits the resolution for large size analytes and which are greater the lower the molecular mass of the matrix and the lower its concentration. On the other hand, the viscosity of a polymer solution increases very rapidly when the molecular mass and the concentration are increased. The application of entangled water-soluble polymer solutions is therefore limited by the very great difficulty, and as a last resort the impossibility, of introducing into a small size capillary (typically less than 100 micrometers) a solution of very high viscosity. Finally, it should be noted that the separation range accessible to capillary electrophoresis may be extended to the largest sizes by the use of pulsed fields. Phenomena of DNA aggregation are encountered in this case which limit the scope of the improvement, and which are also greater, the lower the viscosity of the medium.

To solve the dilemma posed by the search for a low viscosity for injecting the separation medium into the channel, and for resistant topological obstacles for the separation, which in fact lead to a high viscosity, some authors have proposed using a polymer medium whose viscosity decreases considerably during a rise in temperature. This type of medium has the advantage of allowing the injection of the said medium into the capillary at high temperature in a low viscosity state, and separation at a lower temperature in a higher viscosity state exhibiting good separation performance features, as is commonly carried out in gel electrophoresis, in particular with agarose.

In applications WO 94/10561 and WO 95/30782, media are proposed in particular which allow easier injection by raising the temperature. Essentially described in these patent applications are microgels capable of decreasing in volume at high temperature (thus leading to a dilute solution of discontinuous particles of low viscosity) and of swelling at low temperature to the extent of fully occupying the separating channel (thus conferring a gelled character and good separation properties on the medium).

However, these separation media have a viscosity which decreases more or less rapidly with temperature: it is therefore necessary to introduce them into the capillary at a temperature greater than the temperature at which the separation occurs, which may have various disadvantages. On the one hand, in capillary electrophoresis apparatus, it is very difficult to thermostat the entire capillary, and it is therefore difficult to use in an automated fashion a polymer which would only be injectable at a temperature which is markedly greater than room temperature. It would be possible to envisage a solution which is not very viscous at room temperature, and which has a high viscosity and good separation properties at a lower temperature, but that involves carrying out the separations at low temperatures, which is not possible for all analytes. In particular, it is known that for DNA sequencing, an optimum resolution of the "compressions" is obtained at a relatively high temperature (of the order of 50–60° C.), which is incompatible with the preceding principle.

Application WO 98/10274 proposes, for its part, a molecular separation medium comprising at least one type of block copolymer which is in solution at a first temperature and in a gel-type state at a second temperature. This medium comprises, in addition, a buffer whose role is to dissolve the block copolymer at a first temperature, and to cause it to transit towards the gel state at the said second temperature without interrupting the separation process, and without preventing a return to a soluble state during the return to the said first temperature. More specifically, the polymers described are triblock polymers of low molecular massses (typically less than 20,000), of the polyoxyethylene-polyoxypropylene-polyoxyethylene (POE-POP-POE) family and more specifically still ($POE_{99}$-$POP_{69}$-$POE_{99}$, where the subscripts represent the numbers of monomers of each block) (trade name "Pluronic F127"). At low temperature, the two POE segments at the ends of the triblock systems are water-soluble, and given the low molecular mass of the copolymer, the solutions are relatively only slightly viscous up to a high concentration. By raising the temperature to around 15–25° C., the central POP central segment becomes more hydrophobic, and these polymers combine to constitute inside the medium an organized three-dimensional network having a predetermined structure, which confers the appearance and the consistency of a gel on the medium.

Unfortunately, this mechanism exhibits several disadvantages for electrophoresis. On the one hand, it only gives rise to a gel state endowed with good electrophoretic separation properties at high polymer concentrations, greater than 15 g/100 ml or even 20 g/100 ml, which leads to high friction and to long migration times. Moreover, the dependence of the properties as a function of the rate of change in temperature makes the reproducibility of the results unpredictable. Finally, the products proposed in WO 98/10274 exhibit a low viscosity either below room temperature or above room temperature, and exhibit a gel state which is advantageous for electrophoretic separation in the region of room temperature (25° C.), which is not advantageous either for conveniently filling the capillaries, or for applications such as DNA sequencing.

Triblock copolymers having the same structure, with different molecular masses, give rise to comparable physical properties and to performance features in terms of separation which are comparable to or less than F127. Also described in WO 98/10274 is a $POB_{12}$-$POE_{260}$-$POB_{12}$-type polymer, where POB means polyoxybutylene. Unlike the preceding polymers, these polymers give rise to a state which is not very viscous at a temperature greater than room temperature, and to gelling by lowering of the temperature to the region of room temperature.

It should be noted that other polymers exist which may exhibit a thermoviscosity-promoting or thermothickening character in water. Thermoviscosity-promoting polymers are described in Patent Application EP 583 814 which contain, on the one hand, hydrophilic portions of the prepolymer or macromonomer chain type which do not exhibit an LCST in a useful temperature range, and, on the other hand, hydrophilic portions of the prepolymer or macromonomer chain type which exhibit an LCST in the said useful temperature range. However, polymers of this type cannot be used with good performance features as separation medium for electrophoresis for several reasons. On the one hand, they only exert their thermoviscosity-promoting effect in the presence of a relatively large quantity of salt in the solution, between of the order of 0.4 M and several M. This property is highly crippling for electrophoresis, because the use of highly saline solutions leads to heating of the solution and prevents the use of strong electric fields. The separations in highly saline media are therefore slow and of low resolution. Moreover, they exhibit an electrically charged skeleton: if it is desired to use them as electrophoretic separation medium, the polymers constituting the matrix risk being set in motion, or giving rise to electroendoosmosis, disrupting the separation which it is desired to obtain through interaction between the analytes and fixed obstacles. Thirdly, these media are intended to give rise to thermoviscosification or to maintain a roughly constant viscosity in a unique and relatively broad temperature range covering the LCST of the said hydrophilic portions with LCST. However, it would be particularly advantageous, for electrophoresis, to have two clearly distinct useful temperature ranges, one for injecting the separation medium into the capillary, and the other for the actual electrophoretic separation, the said separation being carried out while the medium is maintained at a roughly constant temperature.

In fact, most synthetic media proposed up until now as being capable of giving rise to a thermoviscosifying effect have a charged skeleton (L'Alloret et al., Colloid. Polym. Sci., 273, 1163–1173 (1995), Hourdet, Polymer preprints, 34, 972–973 (1993), Hourdet et al., Polymer, 38, 2535–2547 (1997)). Indeed, a customary way of conferring thermoviscosifying properties on a polymer consists in constructing a molecule having chain portions which are hydrophilic at any temperature and which help to maintain the molecule in solution, and chain portions with LCST which lead, through a rise in temperature, to an attractive interaction between chains, which are responsible for the viscosification. To obtain good viscosification, it would be desirable to multiply the proportion of chains with LCST and their force of interaction, but such an increase also tends to induce a macroscopic phase separation which, by contrast, reduces the viscosity. The presence of electrical charges on the skeleton helps to prevent the macroscopic phase separation through an effect of entropy of the counter-ions or of electrostatic repulsion, and therefore makes it possible to cause entry into the polymer composition of a quantity of portions with LCST which is sufficient to give viscosification, while preventing macroscopic phase separation. It can therefore be seen that it is particularly difficult to constitute thermoviscosifying media based on polymers with a neutral hydrophilic skeleton. A few examples of such media have been described in Vos et al., Polymer, 35, 2644 (1994), but they only give rise to thermoviscosification in the presence of a high salt level and at temperatures of more than 80° C., which also makes them unusable for most of the applications which may be envisaged as a separating matrix, and in particular for electrophoresis.

Consequently, although many types of media, heat sensitive or otherwise, have been proposed as matrices for the electrokinetic separation of species in a channel, and numerous types of heat-sensitive media have also been proposed for other applications, there are currently no media exhibiting optimum properties for the said separations.

SUMMARY OF THE INVENTION

The object of the present invention is precisely to provide a novel type of separation media for which it is found to be possible to optimize the properties as a function of the size of the analytes which it is desired to separate through the selection of a specific copolymer.

DETAILED DESCRIPTION OF THE INVENTION

For the purposes of the invention, the expression separation is intended to cover any method aimed at separating, identifying or analyzing all or some of the species contained in the mixture, the said species being commonly called "analytes".

This separation may thus be carried out in a channel in a microfluidic system or in the context of electrophoresis.

The invention is particularly advantageous in the case of electrokinetic separations.

The expression electrokinetic separation is intended to cover any method aimed at separating all or some of the species contained in a mixture, the said species being commonly called "analytes", by causing them to migrate in a medium under the action of an electric field, whether the field exerts its moving action on the analytes in a direct or indirect manner, for example via a movement of the medium itself, as in electrochromatography, or a movement of ancillary species such as micelles, in the case of micellar electrochromatography, or by any combination of direct or indirect actions. Any method of separation in which the said action of the electric field is combined with another moving action of a nonelectrical origin will also be considered as an electrokinetic separation method according to the invention.

More particularly, the subject of the present invention is a heat-sensitive medium for the separation of species in a separating channel, the said medium comprising an electrolyte in which at least a set of block copolymers is dissolved, characterized in that the said block copolymers:

are provided in the said electrolyte at a sufficient concentration to confer on the said medium the ability to reversibly transit from a viscosity state V1, obtained at a temperature. T1, to a viscosity state V2 which is at least 100% higher than V1, obtained at a temperature T2 which is at least 20° C. higher than T1 and comprising in their structure at least:

two noncontiguous polymeric segments exhibiting an LCST in the said electrolyte and possessing an average number of atoms along their skeleton which is greater than 50, and a polymeric segment which is soluble in the electrolyte at the temperatures T1 and T2.

For the purposes of the invention, unless otherwise explicitly stated, all the average values on sets of chains or on sets of polymeric segments, such as the average molecular mass, or the average number of atoms along the skeleton, or alternatively the average number of grafts in the case of a comb polymer, are understood to mean average values by mass within the usual meaning of polymer physics.

The separation medium claimed therefore possesses the capacity to reversibly transit between a fluid state with a fairly low viscosity so as to allow its introduction into the said channel, obtained at a temperature T1, and a state with a markedly higher viscosity, and in any case at least twice as high, obtained at a temperature T2 which is at least 20° C. higher than the temperature T1. At the temperature T2, the said separation medium is endowed with significant separating properties for species in a predefined range of chemical composition and size.

The expression "temperature T1" is understood to mean, in the context of the invention, either a precise temperature, or a relatively narrow range of temperatures, of a level which is typically of the order of 10° C., useful for carrying out a particular operation relating to the separation process, and in particular for introducing the separating matrix according to the invention into the separating channel. According to a preferred variant of the invention, the temperature T1is between about 15 and 30° C. Likewise, the expression "temperature T2" is understood to mean, in the context of the invention, either a precise temperature or a relatively narrow range of temperatures, of a level which is typically of the order of 10° C., useful for carrying out another particular operation relating to the separation process, and in particular for the step for separating analytes in the channel. According to a preferred variant of the invention, useful for the sequencing of DNA, this temperature or temperature range T2 is between about 40 and 80° C.

According to a preferred variant of the invention, the LCST of a significant fraction of the said segments exhibiting an LCST is between the temperatures T1 and T2 and more preferably between about 20 and 50° C.

For the purposes of the invention, the expression electrolyte is understood to mean a condensed medium capable of conducting ions. In the most common case, this medium is a buffered aqueous medium, such as buffers based on phosphate, tris(hydroxymethyl)amino-methane (TRIS), borate, N-tris(hydroxymethyl)methyl-3-aminopropanesulphonic acid (TAPS), histidine, lysine, and the like. Numerous examples of buffers which can be used in electrophoresis are known to persons skilled in the art, and a number of them are described for example in Sambrook et al., "Molecular Clonning: a laboratory manual", Cold Spring Harbor Lab, New York, 1989. However, any type of electrolyte may be used in the context of the invention, in particular aqueous-organic solvents such as, by way of example, water-acetonitrile, water-formamide or water-urea mixtures, polar organic solvents such as, again by way of example, N-methylformamide. Particularly useful in the context of the invention are the electrolytes termed "sequencing buffers", consisting of an aqueous buffer at alkaline pH supplemented with a substantial proportion of urea and/or of formamide.

For the purposes of the invention, the term "species" is understood to mean analytes in general. These analytes may be particles, organelles or cells, molecular or macromolecular species, and in particular biological macromolecules such as nucleic acids (DNA, RNA, oligonucleotides), nucleic acid analogues obtained by chemical modification or synthesis, proteins, polypeptides, glycopeptides and polysaccharides whose complete or partial separation is desired during their electrokinetic migration within the said separation medium.

For the purposes of the invention, the expression "polymeric segment" or "segment" is understood to mean a set of monomers covalently linked to each other and having specific physicochemical properties, in particular as regards solvation. One example of a polymeric segment for the purposes of the invention is given by a chain of monomers which are all identical (homopolymeric segment), or a copolymer exhibiting no significant correlation in composition over lengths of more than a few monomers (segment of the random copolymer type).

For the purposes of the invention, the expression block copolymer is understood to mean a copolymer consisting of polymeric segments having significantly different compositions, covalently linked to each other. The block copolymer is defined by the fact that each of the segments comprises a sufficient number of monomers so as to exhibit in the electrolyte physicochemical and, in particular, salvation properties which are comparable to those of a homopolymer having the same composition and the same size. It is distinguishable from the random polymer in which the various types of monomer follow each other in an essentially random manner, and locally confer overall properties on the chain which are different from those of the homopolymers of each of the species in question. The size of the homopolymeric segments necessary for obtaining this block character may vary according to the types of monomer and the electrolyte, but it is typically a few tens of atoms along the skeleton of the said segment. It should be noted that it is possible to constitute a block copolymer within the meaning of the invention, in which some or all of the segments themselves consist of a random-type copolymer in so far as it is possible to distinguish within the said block copolymer zones or segments having a size and a difference in chemical composition which are sufficient to give rise, from one segment to another, to a significant variation in the physicochemical, and in particular salvation, properties. Finally, the expression "noncontiguous polymeric segments" within a block polymer is understood to mean two segments linked to each other by a polymeric segment of a different nature.

The block copolymers suitable for the invention possess the feature of combining at least two types of segment in their structures.

The first type of segment is soluble in the electrolyte used for the separation at the two temperatures T1 and T2 for using the claimed medium and preferably do not exhibit an LCST in the said electrolyte. In the present context, the term soluble is understood to refer to solubility in the electrolyte at the temperatures T1 and T2.

On the other hand, the second type of segments is endowed with an LCST in the electrolyte used for the separation. More precisely, this type of segment is essentially soluble in the said electrolyte in a range of low temperatures, and is essentially insoluble in the said electrolyte in a range of high temperatures. The limit between these two temperature ranges is called "minimum demixing temperature" or more commonly "LCST".

By virtue of the presence of these segments with LCST at the level of their structure, the copolymers used according to the invention possess the property of constituting, at low temperature, a macroscopically homogeneous entangled solution in which the interactions between various polymer molecules are essentially repulsive, and of giving rise, following an increase in temperature, to attractive interactions between some of their parts which strengthen the disentangling interactions between chains.

According to a preferred embodiment of the invention, the average number of segments with LCST per copolymer is greater than 2 and preferably greater than 5, and more preferably still of between 8 and 40. By virtue of this large number of segments, capable of interacting in an attractive manner, a given copolymer may interact with numerous other copolymers, which confers high resistance on the medium during the passage of analytes.

The length and the number of segments with LCST present in the copolymers used in the media according to the invention, as well as their chemical nature, may consequently vary significantly in the context of the invention, and may thus greatly cause the viscoelastic properties of the said media to vary considerably according to the desired application, as will be shown more precisely on disclosing the examples of implementation.

The media according to the invention are therefore suitable for producing thermothickening properties. For the purposes of the invention, "thermothickening" refers to a medium having either a thermoviscosifying character, or a thermogelling character.

In accordance with common usage, the term thermoviscosifying is understood to mean a medium remaining in the temperature range(s) for use which is capable of flowing in a macroscopic vessel, in a time compatible with easy handling, that is less than about 30 seconds. By contrast, the expression "gel-type state" is understood to mean a medium incapable of significant flow under the same conditions.

In an equivalent manner, the term thermoviscosifying refers to a medium which does not exhibit in the temperature range(s) for use hysteresis of their properties, or a significant dependence of its properties as a function of the rate of change of temperature, for rates of change of temperature customarily and conveniently used in capillary electrophoresis, that is of the order of 1 degree per minute to about ten degrees per minute. On the other hand, the expression "thermogelling medium", or in an equivalent manner "medium giving rise to a gel-type state" will refer to a medium exhibiting, under these conditions, hysteresis of its properties or else possessing a viscosity greater than 20000 cp.

According to a preferred variant which is particularly suited to the case of automated methods in which it is desired to minimize the time between two consecutive separations, the medium according to the invention will be of the thermoviscosifying type.

According to another preferred variant, when a long waiting time between separations is acceptable and when a maximum resistance of the matrix to the passage of the analytes is desired, a medium according to the invention which gives rise at the temperature T2 to a gel-type state will on the contrary be preferred.

According to a preferred embodiment of the invention, all or some or a significant fraction of the segments with LCST possess along the skeleton an average number of atoms greater than 75, or have a molecular mass greater than 2500, and preferably greater than 4500.

For the purposes of the invention, the expression "a significant fraction", or in an abbreviated form "all or some", is understood to mean a proportion sufficient to give rise, through an increase in temperature, to an increase in viscosity of at least 100% or in an equivalent manner to the multiplication of the viscosity by a factor of 2.

Optimized copolymers for carrying out the invention are in particular those in which the set of segments with LCST represents between 2 and 25% by mass, preferably between 5 and 15% by mass and more preferably still between 8 and 15% by mass of the average total molar mass of the said copolymers, or between 3 and 20% and preferably between 5 and 10% of the total compositon of the copolymers as number of moles of monomers.

The claimed separation medium may advantageously comprise a set of block copolymers comprising a skeleton consisting of a segment or a multiplicity of segments, of an identical or different chemical nature, and exhibiting the common character of being essentially soluble or else solvated in the electrolyte at the temperatures T1 and T2, to which there are covalently linked a multiplicity of segments of an identical or different chemical nature and exhibiting the common characteristic of being essentially soluble or else solvated in the electrolyte at the temperature T1, and essentially insoluble or poorly solvated in the electrolyte at the temperature T2.

All sorts of structures of copolymers of this type may be used for carrying out the invention provided that they have a multiplicity of segments with LCST which are not directly connected, and give rise to reversible thermothickening under the separation conditions.

By way of illustration of various structures which may be adopted by the copolymer according to the invention, there may be mentioned most particularly those where all or part of the said copolymers exist:

in the form of a linear block polymer, in the form of a comb copolymer whose skeleton consists of one or more segments which are soluble in the electrolyte at the temperatures T1 and T2 or else in a branched form.

In the linear block polymer structure, the segments with LCST are present in a number greater than 2 and are separated from each other along an essentially linear skeleton by polymer segments which do not have an LCST. The length of the latter segments may be, in the context of the invention, either relatively uniform or on the contrary variable, the latter variant being preferred.

In fact, it is particularly advantageous to choose a block polymer of the comb polymer type, with a skeleton which is essentially soluble in the electrolyte at the temperatures T1 and T2, carrying a multiplicity of side members which are essentially soluble in the electrolyte at the temperature T1 and insoluble in the electrolyte at the temperature T2. According to a preferred embodiment, the said side members with LCST are arranged along the skeleton in a random or irregular manner.

This embodiment is in general preferable to the opposite structure, which would comprise polymers consisting of a main chain consisting of segments with LCST carrying hydrophilic grafts, in so far as a polymer of this second type contracts above the LCST and thus cannot give rise to a continuous network of topological obstacles necessary for carrying out the invention.

It should be noted that the invention cannot be carried out with block polymers consisting of segments soluble in the electrolyte and of hydrophobic segments without LCST, since such polymers give rise to thermofluidification.

Particularly advantageous in the context of the present invention are separation media in which at least one of the following conditions is satisfied:

all or some of the copolymers possess an average number of atoms, along a soluble section of segment between two consecutive points for binding of said soluble segment with segments with LCST, greater than 210;

all or some of the copolymers possess a molecular mass greater than 30000 or a number of atoms along the main skeleton greater than 2000, and all or some of the copolymers possess a molecular mass between 50000 and 3000000 or a number of atoms along the main skeleton between 2500 and 100000, and/or the average number of segments with LCST per chain is greater than or equal to 4, and is preferably between 5 and 100.

It is particularly advantageous, for carrying out the invention, to use copolymers in which the segment(s) soluble at the temperatures T1 and T2 consist of at least one polymer chosen from polyethers, polyesters such as polyglycolic acid, soluble random copolymers and homopolymers of the polyoxyalkylene type such as polyoxypropylene, polyoxybutylene, polyoxyethylene, polysaccharides, polyvinyl alcohol, polyvinylpyrrol-idone, polyurethanes, polyamides, polysulphonamides, polysulphoxides, polystyrenesulphonate, substituted or unsubstituted polyacrylamide or polymethacrylamide derivatives soluble in the said electrolyte.

By way of illustration of the polyacrylamides and polymethacrylamides, there may be mentioned most particularly polyacrylamide, polyacrylic acid, poly(N,N-dimethylacrylamide) and polyacryloylamidopropanol.

Of course, other polymers soluble in the electrolyte may be used according to the invention as soluble segments, according to the particular application and the ease of introducing them into a block polymer with the desired structure.

It is more generally advantageous for the soluble segments to have a high solvation in the electrolyte at the two temperatures T1 and T2.

Numerous types of polymer may be chosen to constitute the noncontiguous segments with LCST inside a block copolymer which can be used according to the invention, according to the electrolyte envisaged, the preferred temperatures of T1 and T2 for the implementation and the analytes to be separated. Numerous polymers with LCST are known to the person skilled in the art, in particular in aqueous medium. Reference may thus be made to the book "Polymer Handbook" Brandrupt & Immergut, Johy Wiley, New York.

According to a preferred variant of the invention, all or some of the polymeric segments with LCST are derived from one or more polymers chosen from:

polyvinyl alkyl ethers such as polyvinyl methyl ether, hydroxyalkyl celluloses such as hydroxyethyl cellulose and methyl cellulose, homopolymers of ether oxides like polyoxyalkylenes such as polyoxypropylene and polyoxybutylene, random and block copolymers of ether oxides such as copolymers of the polyoxyalkylene type having an LCST like polyoxyethylene/polyoxypropylene and polyoxyethylene/polyoxybutylene, alkylene homo- and copolymers like butylene-propylene, ethylene-propylene and ethylene-butylene, and polyacrylic derivatives derived from the homopolymerization or copolymerization of monomers chosen from acrylic and methacrylic acids, alkyl acrylates and methacrylates such as hydroxypropyl and hydroxyethyl acrylates, N-alkyl-acrylamides or -methacrylamides such as N-ethylacrylamide, N-isopropylacrylamide, N',N-dialkyl-acrylamides or -methacrylamides, arylacrylamides or -methacrylamides and alkylaryl-acrylamides or -methacrylamides.

More preferably, the copolymer used according to the invention comprises at least two noncontiguous segments with an LCST property derived from the homo- or copolymerization of monomers chosen from acrylic and methacrylic acids, N-alkyl-acrylamides or -methacrylamides such as N-ethylacrylamide, N-isopropylacrylamide, arylacrylamides or -methacrylamides and alkylaryl-acrylamides or -methacrylamides.

Thus, it is possible to use, by way of example and without limitation, as segments with LCST, N-isopropyl-acrylamide (NIPAM), N-isopropylmethacrylamide, N,N'-diethylacrylamide, or random copolymers of these monomers with each other or with others.

The following copolymers are most particularly suitable for the invention:

copolymers of the comb copolymer type whose skeleton is of the type including acrylamide, acrylic acid, acryloylaminoethanol or dimethacrylamide and on which there are grafted side segments of the poly(N-alkyl or N,N-dialkyl)acrylamide type, preferably of the poly(N-isopropylacrylamide) type, or side segments of the random or block, polyoxyethylene/oxypropylene copolymer or polyoxypropylene type, or more generally side segments of the polyether type which are notably more hydrophobic than polyoxyethylene copolymers of the block copolymer type exhibiting along their skeleton an alternation of segments of the polyoxyethylene type and of segments of the polyoxypropylene type, or an alternation of segments of the polyoxyethylene type and of segments of the polyoxybutylene type or more generally an alternation of segments of polyethylene and of segments of the polyether type which are notably more hydrophobic than polyoxyethylene.

By way of examples, it is possible to use, as copolymers, in the claimed separation medium, copolymers chosen from polyacrylamide/poly(N-isopropylacrylamide) (PAM-NIPAM); polyvinylalcohol/poly(N-isopropylacrylamide) (PVA-NIPAM), polyoxyethylene/polyoxypropylene, polyacrylamide/oxyethylene-oxypropylene copolymer, polyacrylamide/polyoxypropylene, polyacrylic acid/polyoxypropylene, polyacrylic acid/oxyethylene-oxypropylene copolymer, polyacrylic acid/poly(N-isopropylacrylamide) and polydimethylacrylamide/poly(N-isopropylacrylamide) (PDMAM-NIPAM).

It is possible to advantageously use a medium comprising a comb copolymer carrying along the polyacrylamide skeleton segments with LCST essentially consisting of poly-NIPAM, and comprising along their skeleton a number of carbon atoms between 35 and 600, and the total mass fraction of which does not exceed 25%.

It should also be noted that in the majority of applications, and in particular for separating charged analytes, it is preferable to use a polymer according to the invention which is essentially neutral. It may however be useful in some applications, and in particular for separating weakly charged or uncharged analytes, or analytes which tend to combine with the polymer, to choose a polymer according to the invention which is deliberately charged. It will be possible to conveniently prepare polymers of this type, for example, by allowing a substantial portion of polymerized acrylic acid to be present in the segments soluble in the electrolyte at the temperatures T1 and T2. A copolymer of this type is more particularly described in Example 10 below.

As regards more particularly the copolymer concentration in the medium, it is generally less than 20 g/100 ml by weight. For DNA sequencing applications, it is preferably between about 1 and 8 g/100 ml by weight.

According to a particular embodiment of the invention, the copolymers used in the said medium are advantageously capable, from a concentration of the order of 5 g/100 ml and preferably of the order of 2 g/100 ml by weight, of causing the said medium to reversibly transit from a viscosity state V1, obtained at a temperature T1, to a viscosity state V2 which is at least 100% greater than V1 and which is obtained at a temperature T2 which is at least 20° C. greater than T1.

Also according to a preferred variant of the invention, the viscosity V2 is greater than the viscosity V1 by a factor of at least 5.

As regards the preparation of the copolymers used according to the invention, it may be carried out by any conventional polymerization or polycondensation technique. The choice of the method of preparation is generally carried out while taking into account the structure desired for the copolymer, namely a comb, linear or branched structure, and the chemical nature of the various blocks constituting it.

By way of illustration of these variant preparations, there may be mentioned most particularly the processes according to which the said copolymers are obtained by:

ionic or free-radical polycondensation, polymerization or copolymerization of identical or different monomers, of identical or different macromonomers, or of a mixture of identical or different monomers and macromonomers, or by grafting several polymeric segments with LCST onto a linear or branched polymeric skeleton which is essentially of the soluble type, or by polymerization of polymeric side segments with LCST from a linear or branched polymeric skeleton which is essentially of the soluble type.

Preferably, all or some of the copolymers used according to the invention are obtained by:

a) copolymerization of monomers which are essentially of the soluble type and of macromonomers which are essentially of the type with LCST comprising a reactive functional group at least at one of their ends, or b) copolymerization of macromonomers which are essentially of the type with LCST comprising a reactive functional group at least at one of their ends, and macromonomers which are essentially of the soluble type comprising at least one reactive functional group in their structure.

For the purposes of the invention, the expression reactive functional group is understood to mean a group allowing the molecule carrying this group to be integrated into the macromolecule during the copolymerization reaction without interrupting the said copolymerization.

Using the preferred methods and rules set out above, persons skilled in the art are capable of preparing copolymers in accordance with the invention by adapting the structure, the nature and the method of preparation of the said polymers according to the separation properties desired for one application or another.

By way of nonlimiting illustration of the claimed separation media mention may be most particularly be made of the following media:

the media transiting from a viscosity V1 of between 50 and 1000 $mPa.m^{-1}$ at a temperature T1 of between 15 and 30° C. to a viscosity V2 which is greater than V1 by a factor of between 2 and 50 at a temperature T2 of the order of 40° C. or higher and comprising between 5 g/100 ml and 20 g/100 ml of copolymers possessing an average molecular mass of between 30000 and 2000000 or a number of atoms along the main skeleton of between 1000 and 60000, a fraction by mass of segments with LCST of between 2% and 20%, and an average molecular mass of the segments with LCST of between 2000 and 20000 or an avarage number of atoms along a segment with LCST of between 35 and 350;

the media transiting from a viscosity V1 of between 100 and 10000 $mPa.m^{-1}$ at a temperature T1 of between 15 and 30° C. to a viscosity V2 which is greater than V1 by a factor of between 2 and 100 at a temperature T2 higher than 40° C. and comprising between 1 g/100 ml and 80 g/100 ml of copolymers possessing:

an average molecular mass of between 500000 and 5000000 or a number of atoms along the main skeleton of between 7000 and 90000, a fraction by mass of segments with LCST of between 2.5% and 15%, and an average molecular mass of segments with LCST of between 4000 and 30000 or an average number of atoms along a segment with LCST of between 60 and 600; and the media transiting from a viscosity V1 of between 100 and 10000 mPa.m$^{-1}$.s$^{-1}$ at a temperature T1 of between 15 and 30° C. to a viscosity V2 which is greater than V1 by a factor of between 2 and 100 at a temperature T2 of the order of 40° C. or higher and comprising between 0.1 g/100 ml and 5 g/100 ml of copolymers possessing an average molecular mass greater than 500000 or a number of atoms along the main skeleton greater than 7000, a fraction by mass of segments with LCST of between 2% and 15%, and an average molecular mass of the segments with LCST greater than 4000 or an average number of atoms along a segment with LCST greater than 90.

In the present description, the viscosity is that obtained at a shear rate of 10 s$^{-1}$.

It is also possible, in the context of the invention, to include in the separation medium, in addition to the copolymer(s) with a thermothickening character, other species not exhibiting these properties, such as in particular water-soluble polymers, nonthermothickening associative polymers, or else neutral or ionic surfactants, provided that these adjuvants do not give rise to demixing in the separation medium or to a loss of the reversible thermothickening character. Such adjuvants may be advantageous for modulating the properties and/or the separating power of the said medium. It is in particular known that the addition of certain surfactants may in some cases reinforce the association between polymers, and therefore the thermothickening character. It may also be advantageous to add to the medium associative or nonassociative polymers of low molecular weight in order to enhance the separation of the smallest analytes contained in a mixture without adversely affecting the overall viscosity, as is known in contexts different from that of the invention.

The subject of the present invention is also the use of a separation medium as defined above for the separation or analysis of species among molecular or macromolecular species, and in particular biological macromolecules such as nucleic acids (DNA, RNA, oligonucleotides), nucleic acid analogues obtained by chemical synthesis or modification, proteins, polypeptides, glycopeptides and polysaccharides, organic molecules, synthetic macromolecules or particles such as mineral particles, latex, cells or organelles.

It is particularly useful for the sequencing of DNA, for which it makes it possible to obtain optimum separation conditions linked to a high viscosity, to a high temperature for which the resolution of compressions is good and the separation rapid, while preserving, at room temperature, a moderate viscosity allowing easy injection of DNA.

However, the possibility offered by the invention of considerably varying the viscosity of the medium by changing temperature is also advantageous for other applications.

It is in particular advantageous every time an increase in the rigidity or the viscosity of the medium contained in a capillary or a microchannel might be desirable. For example, a high viscosity makes it possible to reduce the electrohydrodynamic effects responsible for a poor separation of large DNAs in a pulsed field and more generally to reduce the damaging hydrodynamic flows in a capillary or a microchannel.

It should also be noted that although the media according to the invention in general best exert their beneficial effect by means of a change in temperature, they are also suitable for use at constant temperature. They may thus be suitable for introduction into the separating channel and for the consecutive separation of analytes at the same temperature. This may be advantageous in particular if an apparatus is available which is capable of introducing into the separating channel a medium of high viscosity, and/or which does not make it possible to easily modify the temperature between the introduction of the said medium into the channel and the separation of the analytes.

Another advantage of the high viscosities allowed by the media according to the invention is that they reduce electroosmosis (see for example Bello et al., Electrophoresis 15, 623, 1994), without a need to use other methods for suppressing electroosmosis known to persons skilled in the art, such as for example the use of polymers having affinity for the wall of the capillary, or else the grafting of neutral hydrophilic polymers onto the surface. If the suppression of electroosmosis or the interaction of the analytes with the walls produced by the media according to the invention is not sufficient for a particular application, it is possible to combine the invention with one of these processes known to persons skilled in the art, and to thus obtain properties which are even better than those obtained with these methods used alone.

Advantageously, it is possible to modulate the separating properties of the claimed medium via the selection of a copolymer in accordance with the invention and whose thermothickening effect is more particularly optimized for the separation of species of different sizes.

By way of illustration of this type of adaptation which is accessible according to the invention, it is possible in particular:

to separate molecules having a molecular mass of less than 50000 or oligonucleotides comprising less than 100 nucleotides, or else native or denatured proteins with a medium transiting from a viscosity V1 of between 50 and 1000 mPa.m$^{-1}$.s$^{-1}$ at a temperature T1 of between 15 and 30° C. to a viscosity V2 which is greater than V1 by a factor of between 2 and 50 at a temperature T2 of the order of 40° C. or higher and comprising between 5 g/100 ml and 20 g/100 ml of copolymers possessing:

an average molecular mass of between 30000 and 2000000 or a number of atoms along the main skeleton of between 1000 and 60000, a fraction by mass of segments with LCST of between 2% and 20%, and an average molecular mass of the segments with LCST of between 2000 and 20000 or an avarage number of atoms along a segment with LCST of between 35 and 350, to separate products of reaction of DNA sequence, DNA duplexes of less than 1000 base pairs, denatured proteins or synthetic or natural polymers having a molecular mass of between 20000 and 10000000 with a medium transiting from a viscosity V1 of between 100 and 10000 mpa.m$^{-1}$.s$^{-1}$ at a temperature T1 of between 15 and 30° C. to a viscosity V2 which is greater than V1 by a factor of between 2 and 100 at a temperature T2 higher than 40° C. and comprising between 1 g/100 ml and 8 g/100 ml of copolymers possessing:

an average molecular mass of between 500000 and 5000000 or a number of atoms along the main skeleton of between 7000 and 60000, a fraction by mass of segments with LCST of between 2.5% and 15%, and an average molecular mass of segments with LCST of between 4000 and 30000 or an average number of atoms along a segment with LCST of between 60 and 600 or to separate DNA duplexes having a size of between 500 bases and several millions of base pairs, or particles such as latexes, whole cells, whole chromosomes or organelles with a medium transiting from a viscosity V1 of between 100 and 10000 $mPa.m^{-1}.s^{-1}$ at a temperature T1 of between 15 and 30° C. to a viscosity V2 which is greater than V1 by a factor of between 2 and 100 at a temperature T2 of the order of 40° C. or higher and comprising between 0.1 g/100 ml and 5 g/100 ml of copolymers possessing:

an average molecular mass greater than 500000 or a number of atoms along the main skeleton greater than 7000, a fraction by mass of segments with LCST of between 2% and 15%, and an average molecular mass of the segments with LCST greater than 4000 or an average number of atoms along a segment with LCST greater than 90.

More preferably, these media comprise a set of copolymers chosen from:

copolymers of the comb copolymer type whose skeleton is of the acrylamide, acryloylamino-ethanol or dimethylacrylamide type and on which side chains of the poly(N-isopropylacrylamide) type are grafted, and copolymers of the block copolymer type and which exhibit along their skeleton an alternation of blocks of the polyoxyethylene type and blocks of the polyoxypropylene type, or an alternation of blocks of the polyoxyethylene type and of blocks of the polyoxybutylene type, or more generally an alternation of blocks of the soluble polyoxyalkylene type and of polyoxyalkylene blocks with LCST.

By way of illustration of the method of using the claimed separation medium there may be proposed in particular that comprising:

selecting a separation medium according to the invention, according to the characteristics of the species to be separated;

introducing this medium into a separating channel of an electrophoresis apparatus in a sufficient quantity to constitute its separation medium;

placing a significant proportion of the channel at the temperature T2, either prior to or following the introduction of a sample;

introducing a quantity of sample at the inlet of the separating channel;

carrying out the separation at a temperature of the order of T2 in the thermostated portion of the channel; and detecting the migration of the analytes initially contained in the sample.

This detection involves conventional techniques which fall within the competence of persons skilled in the art and will not therefore be detailed in the present description.

It should be noted that the use of the claimed medium also covers variants in which the temperature is modified during the separation stage since the said variation in temperature comprises a temperature or a range of temperatures T2 at which the thermothickening of the medium is carried out as defined above, as well as the variants in which the above cycle is repeated any number of times, preferably in an automated fashion.

In fact, the invention is particularly advantageous in the case of automated electrokinetic separations since it allows automated filling of the separating channel more easily and more rapidly. Moreover, the introduction of the sample may, in the context of the invention, be carried out before, during or after heating a significant portion of the separating channel to the temperature T2.

The subject of the present invention is also the capillary electrophoresis devices, including those based on chips, using, as separation medium, a medium in accordance with the invention. It is particularly useful in the case of electrophoresis devices termed "chip-based" or etched microchannel-based, since, in general, it is more difficult for these devices to tolerate the application of high pressure values for introducing the separation medium than cylindrical capillaries.

The media according to the invention and the separation methods using these media are particularly advantageous for diagnostic, genotyping, high-throughput-screening and quality control applications, or for detecting the presence of genetically modified organisms in a product.

The figures and examples given below are presented by way of nonlimiting illustration of the present invention.

FIGURES

FIG. 1: Variation of the viscosity as a function of the temperature for various copolymers PAM-NIPAM and PDMA-NIPAM, and for a conventional polyacrylamide in solution at 5 g/100 ml in water.

Figure 2A:
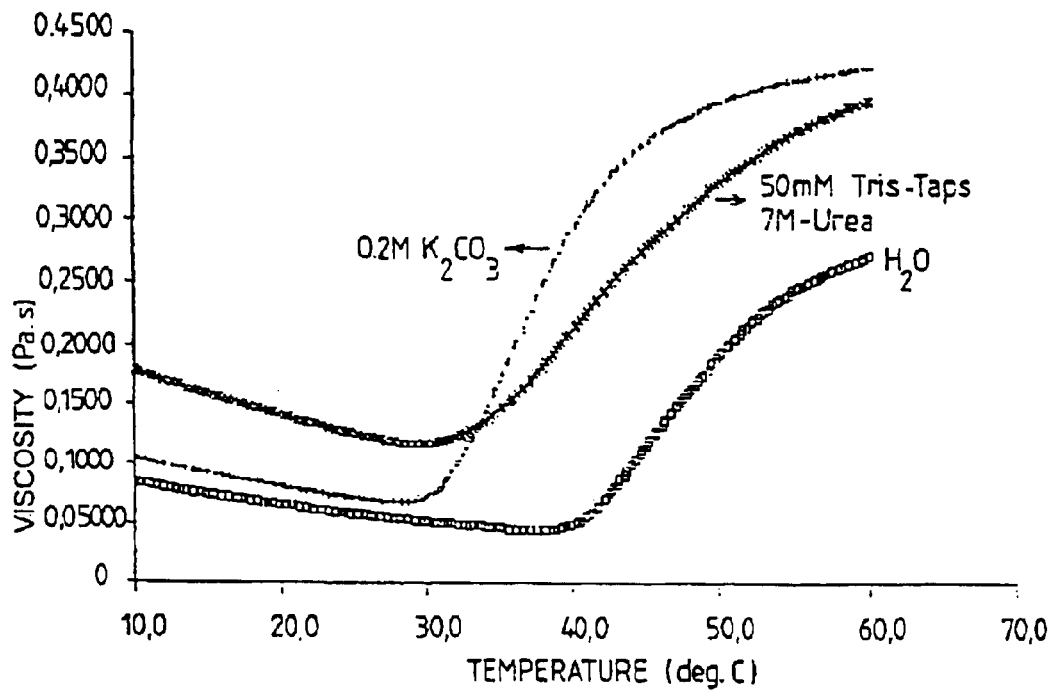
Figure 2B:
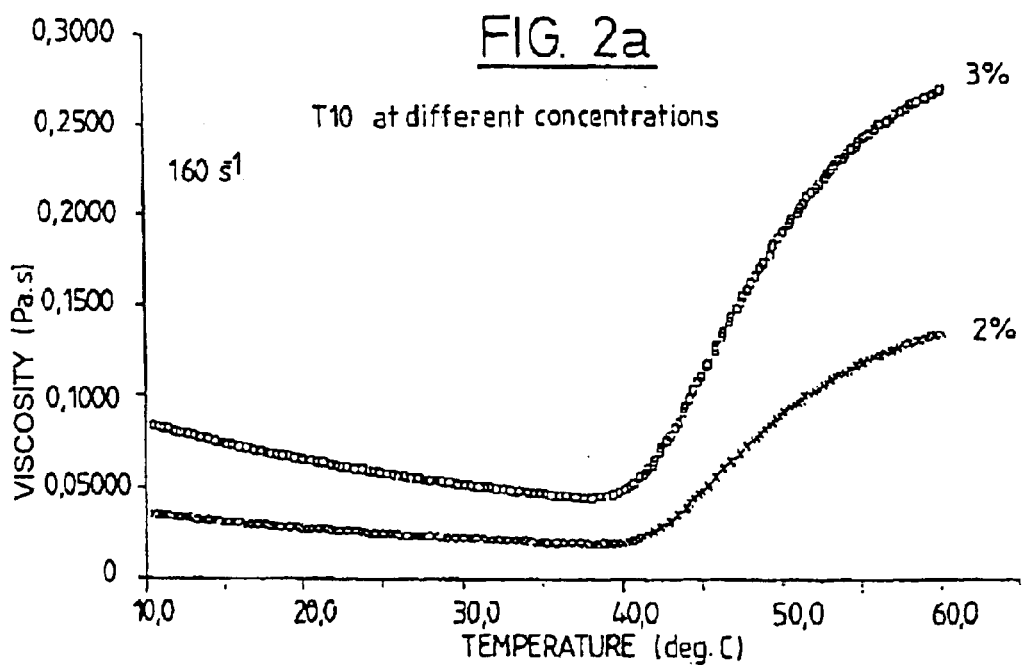

FIG. 2: Variation of the viscosity as a function of the temperature for copolymers according to the invention the copolymer PAM-NIPAM T10, in water, in a 0.2M $K_2CO_3$ buffer and a 50 mM Tris-Taps buffer, 7M urea which can be used for the sequencing of DNA (FIG. 2a), and a copolymer PAM-NIPAM at two different concentrations (2 and 3 g/100 ml) (FIG. 2b).

Figure 3A:
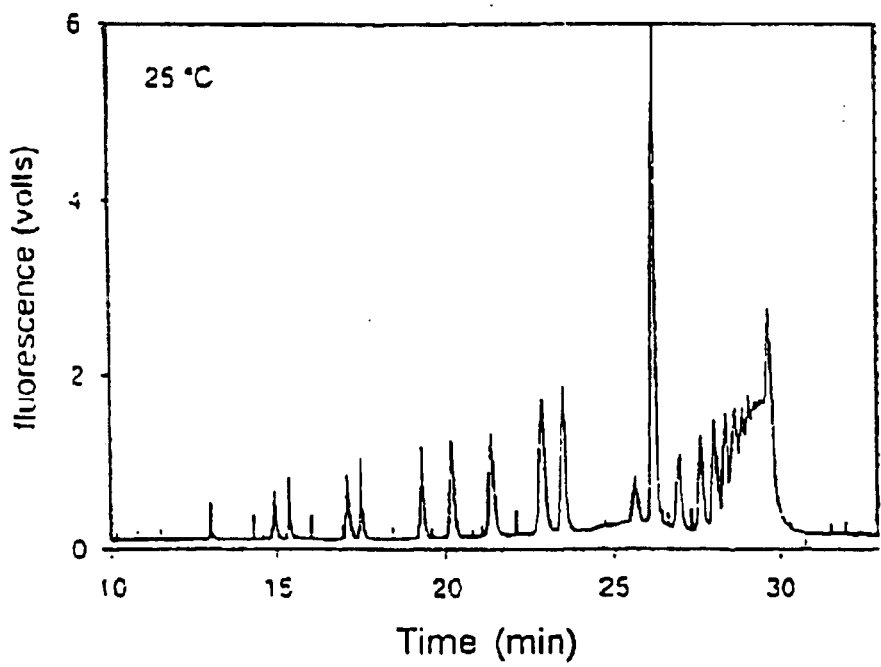
Figure 3B:
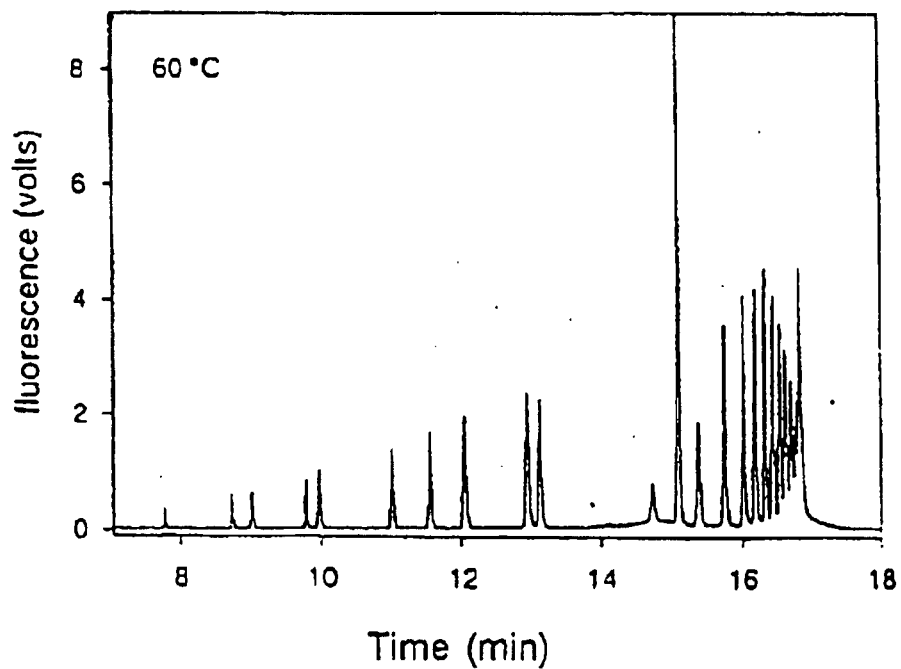

FIG. 3: Example of separation of duplex DNA fragments in the 100–12000 base pair size range ("kb ladder", Life Technologies, Paisley, UK) in a separation medium according to the invention based on a polymer PAM-NIPAM (T15) in solution at 2 g/100 ml in a TRIS-TAPS buffer at 25° C. (FIG. 3a) and 60° C. (FIG. 3b).

Figure 4A:
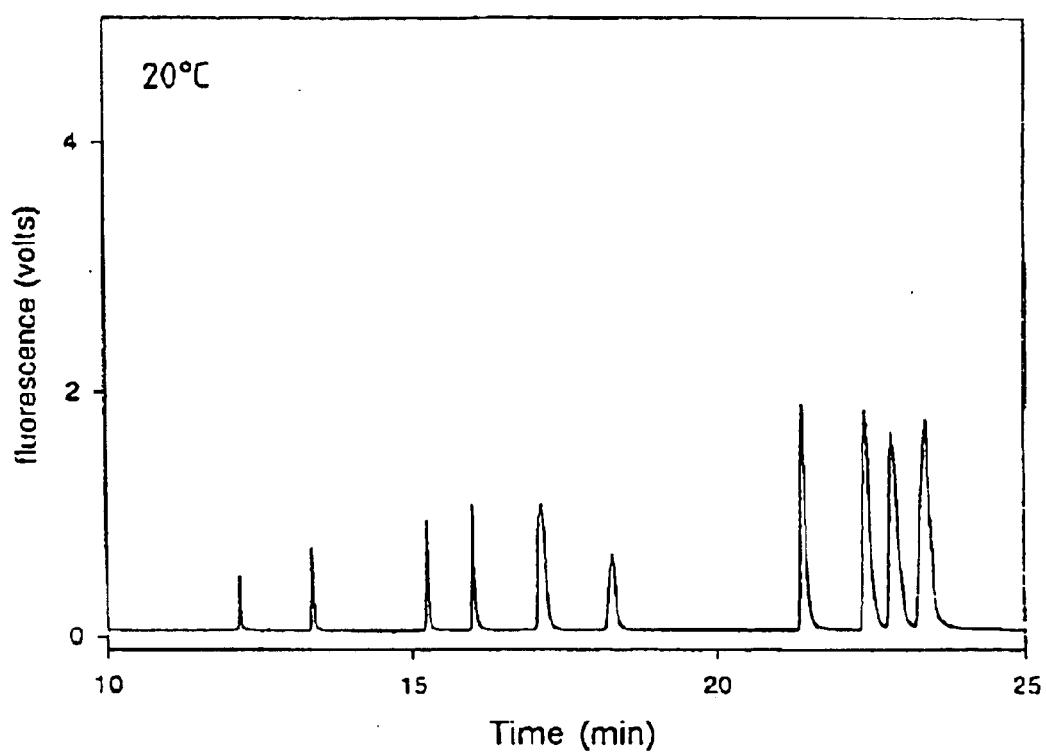
Figure 4B:
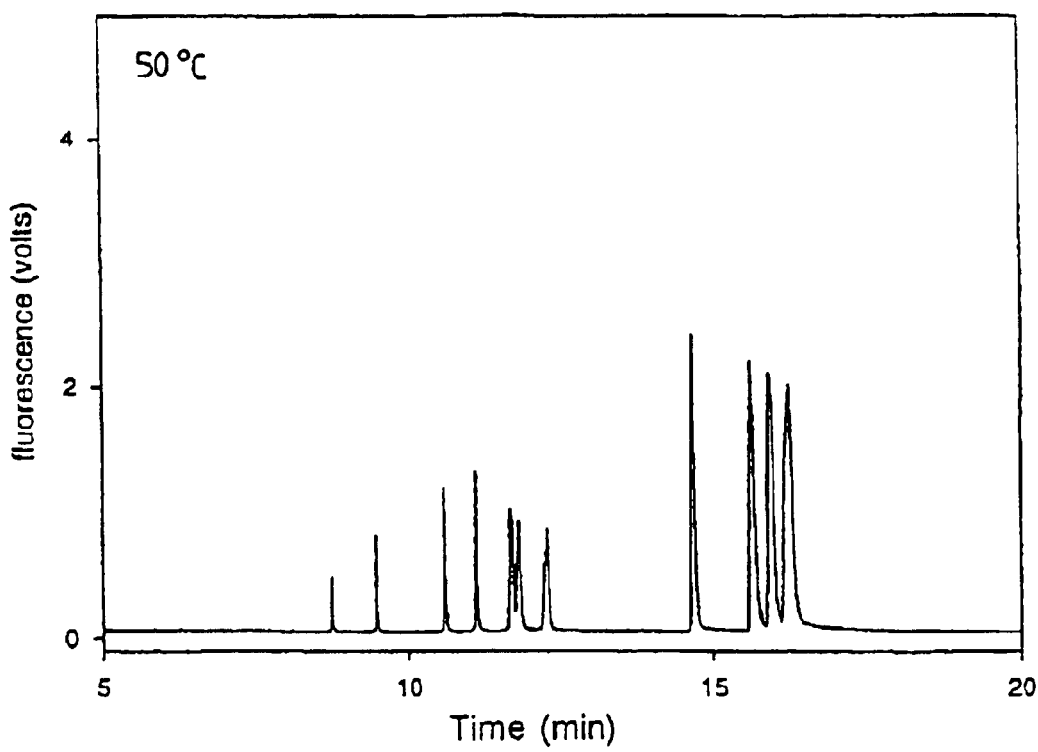

FIG. 4: Electrophoretograms representing the separation of restriction fragments "PhiX-174-RF DNA Hae III digest" (Pharmacia, biotech) in a medium according to the invention obtained based on polymer T7, at 20° C. (FIG. 4a) and at 50° C. (FIG. 4b).

Figure 5A:
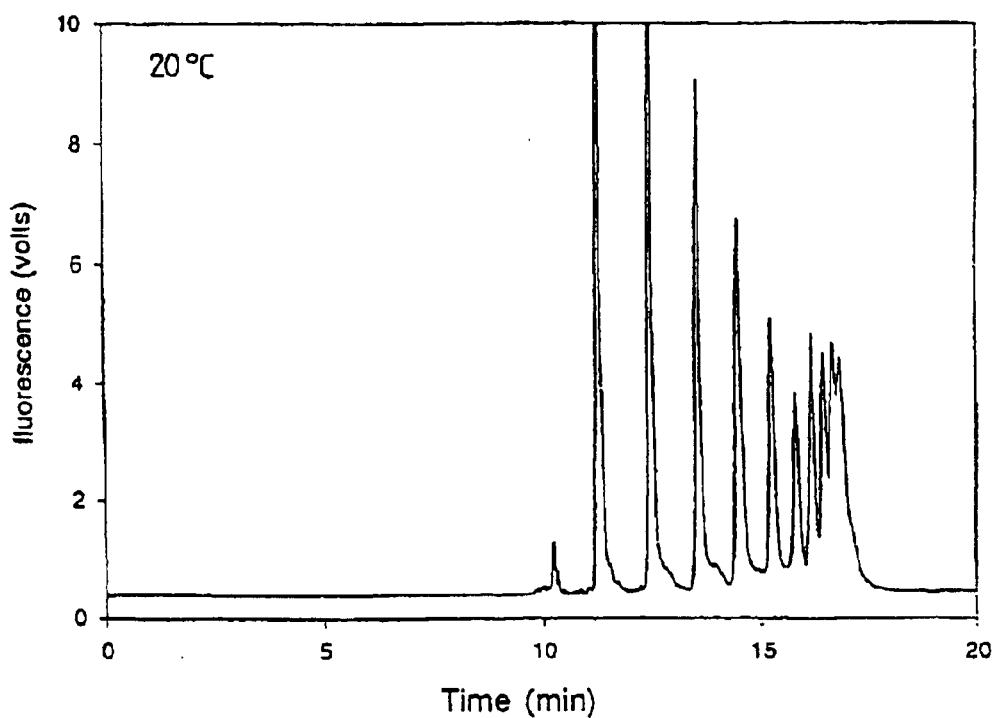
Figure 5B:
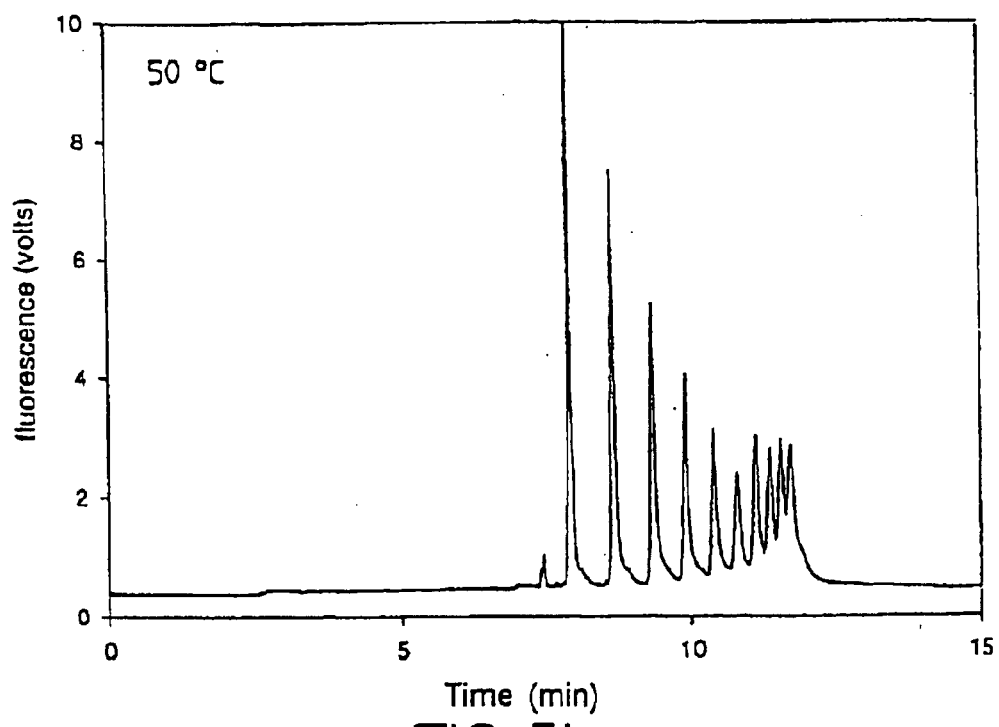

FIG. 5: Example of separation of duplex DNA fragments (100 bp fluorescein ruler, Bio-Rad) in a separation medium according to the invention based on T21 at two temperatures, 20° C. (FIG. 5a) and 60° C. (FIG. 5b).

Figure 6A:
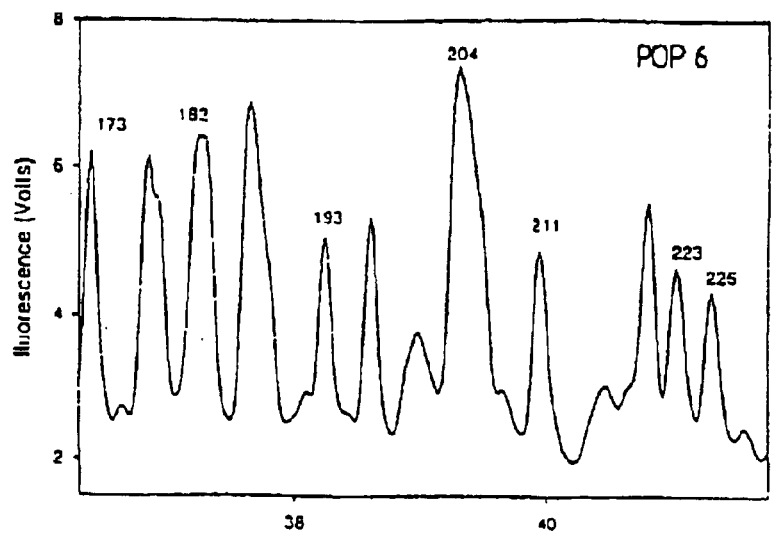
Figure 6B:
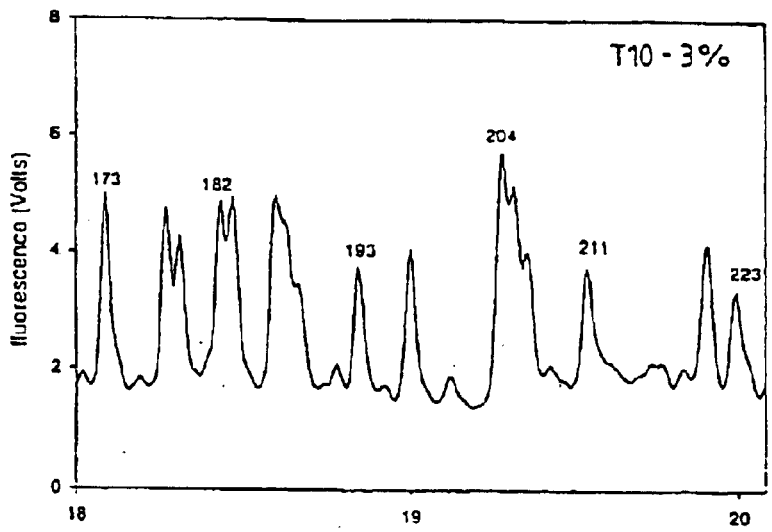
Figure 6C:
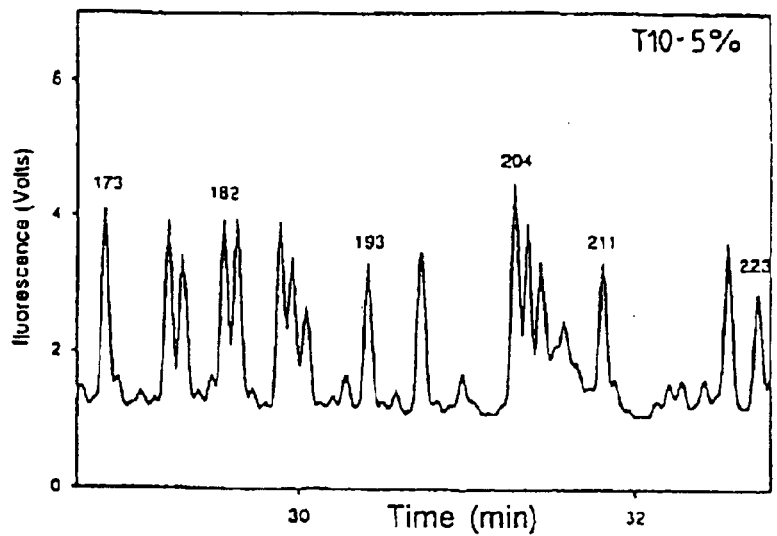

FIG. 6: Portions of electrophoretograms representing the separation of a product of reaction of a sequence, obtained with a medium according to the invention based on a copolymer PAM-NIPAM (T10) at 5 g/100 ml in TRIS-TAPS buffer, 7M urea at 60° C. (FIG. 6c), PAM-NIPAM (T10) at 3 g/100 ml (FIG. 6b) and with a commercial sequencing medium (POP6 Perkin-Elmer) (FIG. 6a).

Figure 7A:
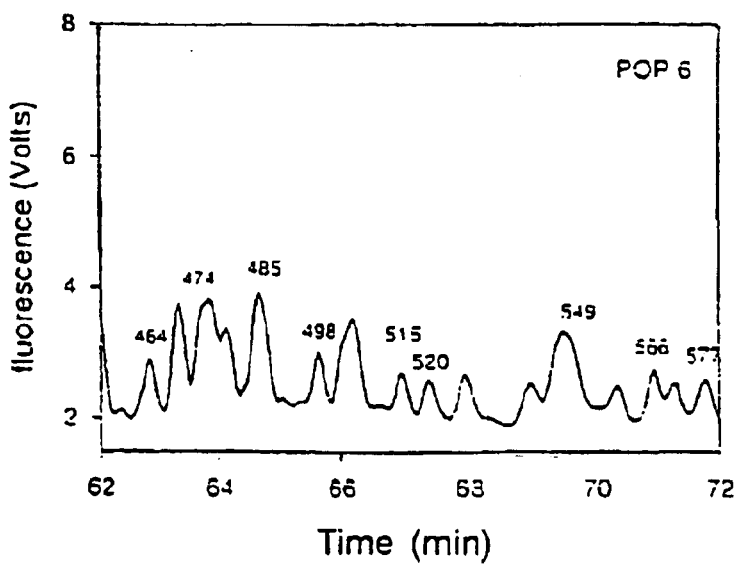
Figure 7B:
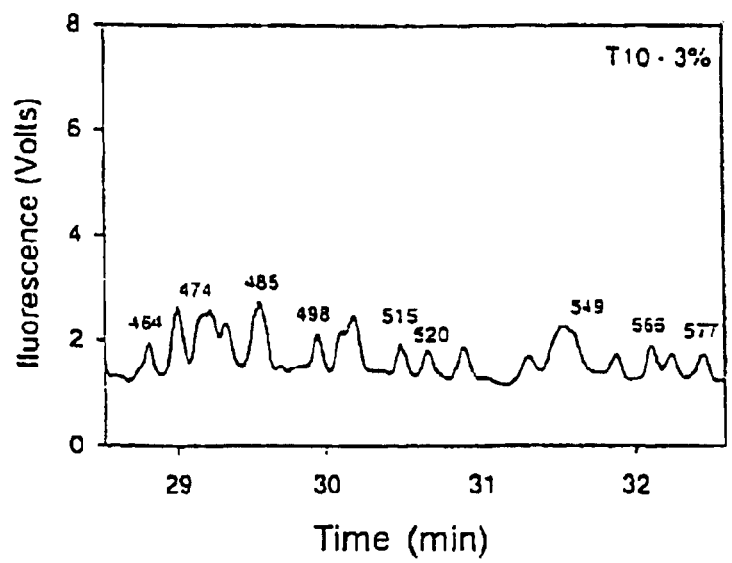
Figure 7C:
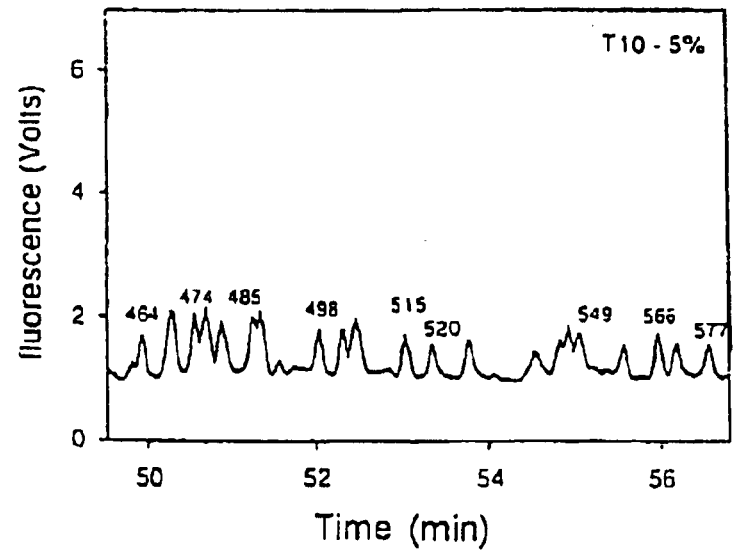

FIG. 7: Portions of electrophoretograms representing the separation of a product of reaction of a sequence, obtained with a medium according to the invention based on a copolymer PAM-NIPAM (T10) at 5 g/100 ml in TRIS-TAPS buffer, 7M urea at 60° C. (FIG. 7c), PAM-NIPAM (T10) at 3 g/100 ml (FIG. 7b) and with a commercial sequencing medium (POP6 Perkin-Elmer) (FIG. 7a).

Figure 8:
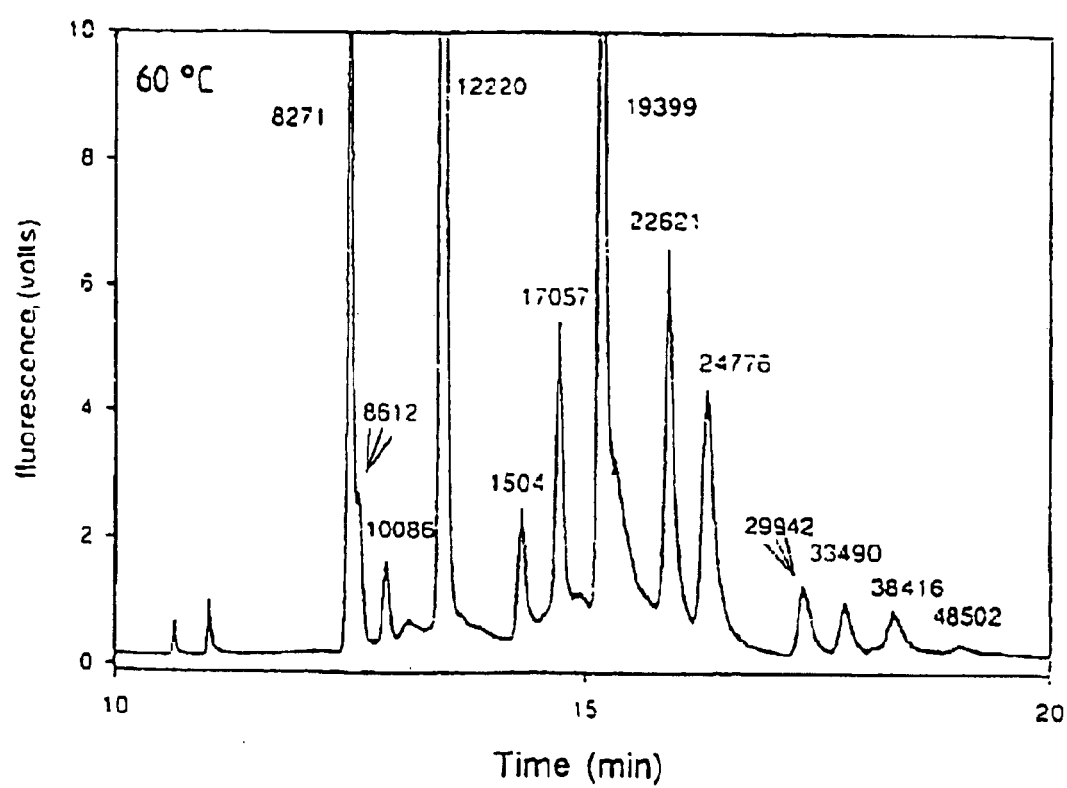

FIG. 8: Electrophoretogram representing the separation of large duplex DNA "high Mw markers" (Life Technologies, Paisley, GB), by pulsed electrophoresis in a medium according to the invention obtained based on polymer T10 at 60° C.

FIG. 9: Variation of the viscosity as a function of the temperature for
- a copolymer PVA-NIPAM, compared with that of a polymer PVA, and
- a copolymer POP-POE-POP in relation to that of the polymer POE at a concentration of 5 g/100 ml.

Figure 10A:
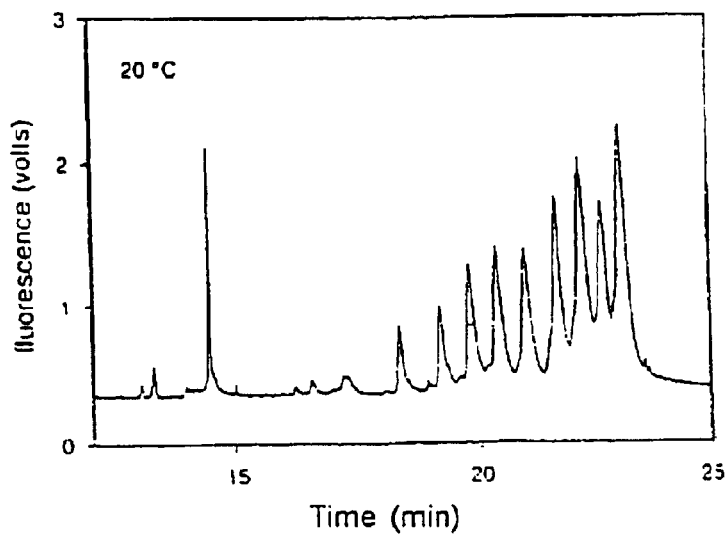
Figure 10B:
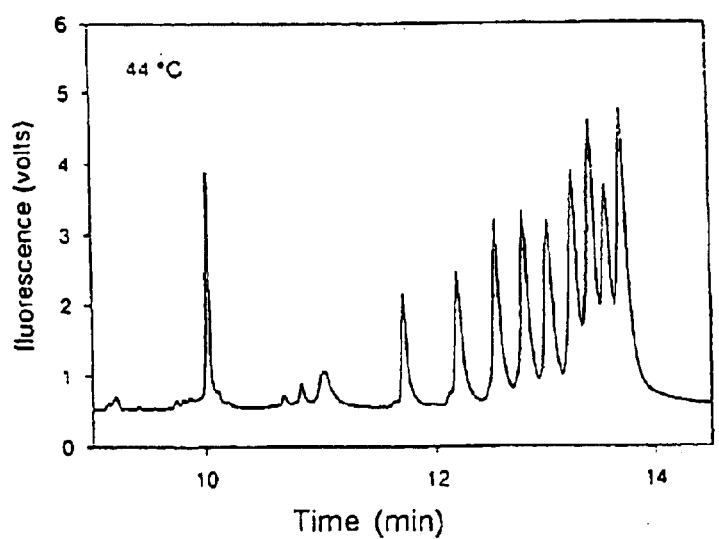

FIG. 10: Example of separation of duplex DNA fragments in the 50–500 base pair size range (sizer 50–500 bp, Pharmacia biotech) in a separation medium according to the invention based on PVA-NIPAM at two temperatures, 20° C. (FIG. 10a) and 40° C. (FIG. 10b).

Figure 11A:
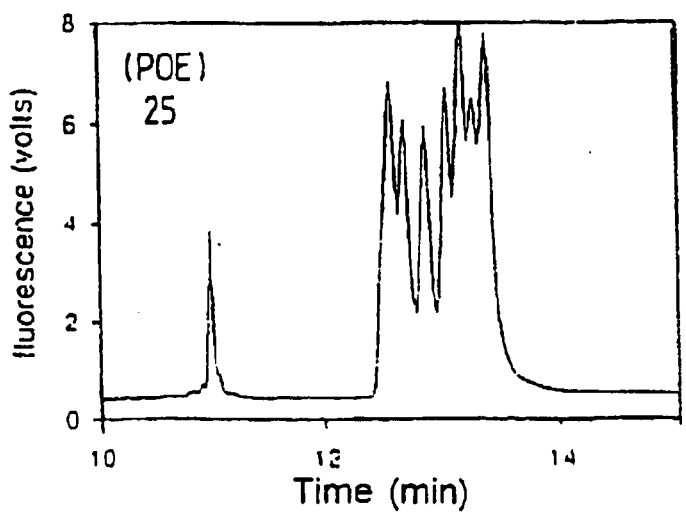
Figure 11B:
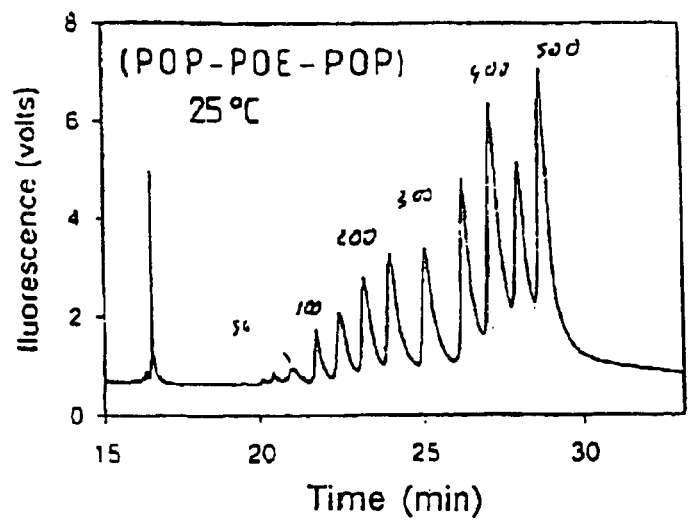
Figure 11C:
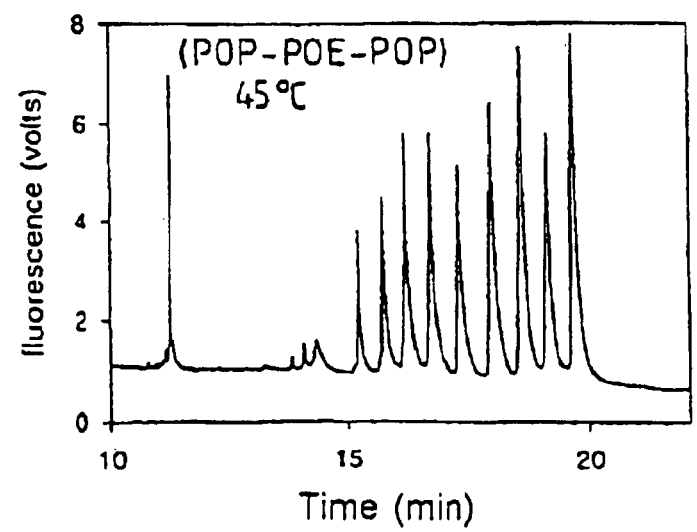

FIG. 11: Electrophoretograms representing the separation of the sizer 50–500 bp, Pharmacia biotech, which are obtained in a medium based on POE (FIG. 11a), based on POP-POE-POP at 25° C. (FIG. 11b) and based on POP-POE-POP at 45° C. (FIG. 11c).

Figure 12:
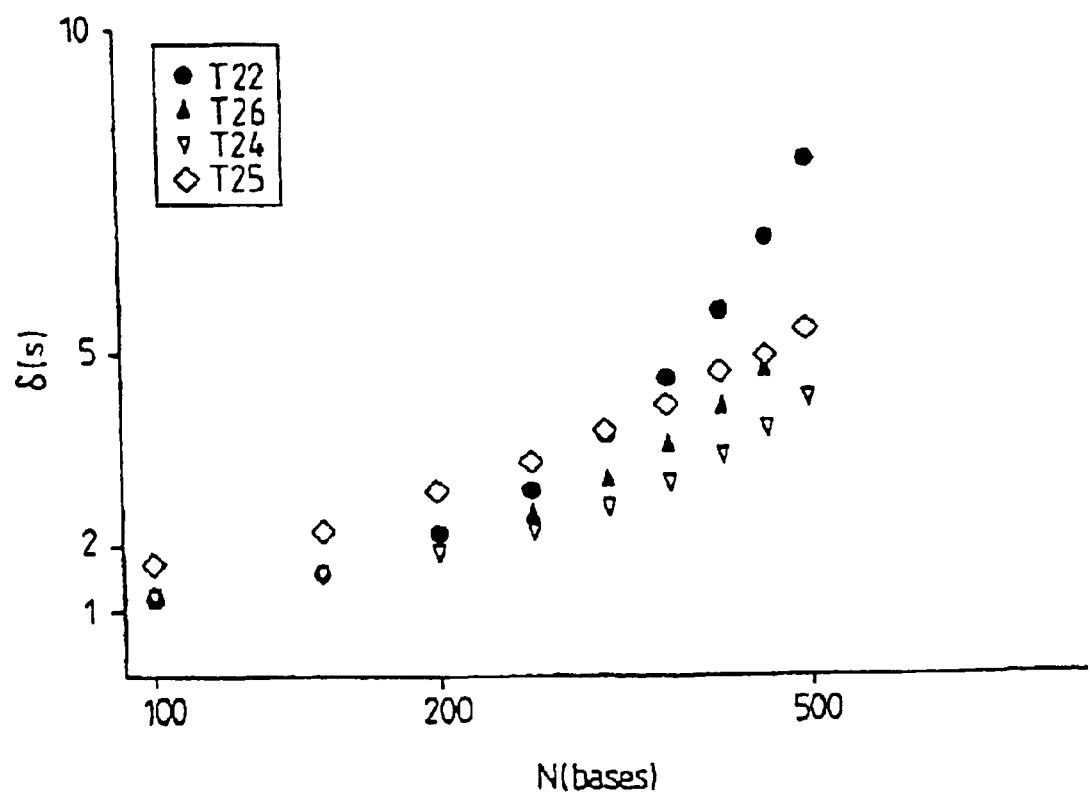

FIG. 12: Band widths for a.series of separations of single-stranded DNA fragments in denaturing medium (fluorescein 50 bp ladder, Pharmacia Biotech), in media according to the invention which can be differentiated by the average number and the average length of the segments with LCST: smaller band widths correspond to a better separation.

EXAMPLE 1

Preparation of a macromonomer with LCST of pNIPAM which is nonfunctionalized, having a molecular mass in the region of 10000, for the preparation of a thermogelling copolymer in accordance with the invention.

1) Polymerization of NIPAM

The free-radical polymerization of NIPAM is carried out in pure water, at a temperature slightly higher than room temperature but less than the LCST of the polymer. The initiator is a redox pair in which the oxidizing agent is potassium persulphate, $K_2S_2O_8$ (KPS), and the reducing agent is aminoethanethiol, AET.HCl. The priming reaction is:

$K_2S_2O_8 + 2Cl^-, NH_3^+—CH_2CH_2—SH \rightarrow 2KHSO_4 + 2Cl^-, HN_3^+—CH_2—CH_2—S.$ The AET.HCl also plays the role of transfer agent, which makes it possible to control the length of the chains.

Procedure 20 g of NIPAM (0.18 mol) and 200 ml of water are introduced into a 500 ml three-necked flask surmounted by a condenser and equipped with a device for admitting nitrogen. The mixture is then stirred and heated to 29° C. by a water bath. Nitrogen bubbling is initiated. After 45 minutes, 0.42 g of AET.HCl (0.0037 mol), previously dissolved in 20 ml of water, is added, followed by 0.0018 mol of potassium persulphate (KPS) dissolved in a minimum quantity of water. The mixture is kept stirring for 3 hours. The solution is then concentrated and then freeze-dried.

To isolate the polymer, precipitation is carried out according to the following procedure:

The solid obtained is redissolved in 100 ml of methanol, the hydrochloride present is neutralized by addition of 0.0037 mol of KOH (that is 0.208 g dissolved in about 25 ml of methanol) incorporated dropwise into the solution. The salt formed, KCl, precipitates and is extracted by filtration. The filtrate thus recovered is concentrated and then poured dropwise into 4 liters of ether. The polymer precipitates and is recovered by filtration on No. 4 sintered glass. The solid is then dried under vacuum produced by a slide vane rotary vacuum pump. The mass yield is of the order of 50%.

The above protocol leads to an aminated polymer "PNIPAM-A-10", and corresponds to initiator-monomer ratios Ro=0.02 and Ao=0.01, where:

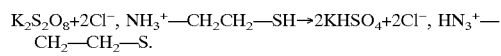

Ro=[R—SH]/[NIPAM] and Ao=[KPS]/[NIPAM].

Various other aminated polymers were prepared according to the same protocol by varying the polymerization temperature and the ratio Ro, while maintaining a ratio Ao of 0.01. These polymers are described and defined in Table 1.

2) Modification of the Aminated PNIPAM for Its Copolymerization with One or More Segments which Are Soluble at the Temperatures T1 and T2

The PNIPAM macromolecules synthesized have amine functional groups at the chain ends, the latter being derived from the initiator aminoethanethiol AET.HCl.

By reacting the amine functional group with acrylic acid, a vinyl double bond is attached at the end of the chain according to the following reaction scheme:

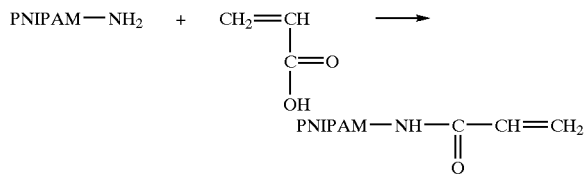

Procedure 50 ml of methylene chloride, 1.5 g of acrylic acid (0.021 mol), 9 g of PNIPAM and 4.3 g of dicyclohexyl-carbodiimide (DCCP) (0.21 mol) are introduced into a 100 ml beaker.

The reaction medium is stirred for one hour. As the acrylic acid is in great excess relative to the PNIPAM (the quantity of acrylic acid is about twenty times that of the PNIPAM), it can be assumed that all the amino functional groups have been modified, which will be confirmed by the copolymerizations described in Example 2. The mixture is then filtered on No. 4 sintered glass in order to remove the dicyclohexylurea precipitate, a by-product resulting from the conversion of the DCCI.

The mixture is then concentrated to 15 ml and then poured dropwise into 200 ml of ether in order to precipitate the polymer. The mixture is filtered on No. 4 sintered glass and the solid is washed with three times 100 ml of ether and then it is dried under vacuum produced by a slide vane rotary vacuum pump overnight.

A poly-(NIPAM) macromonomer carrying an allyl functional group at the chain end is thus obtained with a mass yield of the order of 70%.

The molar masses of the macromonomers thus prepared were measured by SEC (steric exclusion chromatography) under the following conditions:

a: a 0.5 M aqueous $LiNO_3$ solution at 20° C. using 4 Shodex Pack B803 to B806 columns of 25 cm in series, with refractometric detection and calibration of the molecular masses relative to a POE standard b in THF at 40° C., with an ultrastyragel column, double refractrometric detection and universal calibration relative to polystyrene samples. This second mode of determination is more accurate because on the one hand, the universal calibration dispenses with the difference in flexibility between the chains of the polymer to be studied and the standards, and on the other hand because THF is a better solvent for PNIPAM than water.

TABLE 1

| Molecular mass | PNIPAM-C | PNIPAM-5 | PNIPAM-M | PNIPAM-10 | PNIPAM-L | PNIPAM-20 |
|---|---|---|---|---|---|---|
| Preparation conditions | Ro = 0.03 23° C. | Ro = 0.025 23° C. | Ro = 0.02 25° C. | Ro = 0.02 29° C. | Ro = 0.015 25° C. | Ro = 0.01 25° C. |
| Mw (g/mol) (b) | 10800 | 12800 | 15800 | 20400 | 23000 | 34000 |
| Average number of atoms along the chain (b) | 200 | 230 | 290 | 370 | 420 | 620 |
| Polydispersity (Mw/Mn) (b) | 5.7 | 2.0 | 4.2 | 3.2 | 4.9 | 5 |
| Mw (g/mol) (a) | | 4500 | | | | 21000 |
| Polydispersity (Mw/Mn) (a) | | 1.6 | | | | 4.6 |

These results show that it is possible to vary the average molecular mass of the macromonomers by varying the polymerization temperature, and the initiator/polymer ratio Ro, the highest ratios Ro leading to the lowest molecular masses. They also show that the polydispersity values of the macromonomers are high, in general greater than 2.

EXAMPLE 2

Preparation of various copolymers with a comb structure and comprising, as segments with LCST, the PNIPAMs prepared in Example 1.

The aim of this example is the preparation of copolymers according to the invention by copolymerization of macromonomer(s) PNIPAM obtained according to Example 1 with water-soluble-type monomers.

a) Synthesis

This copolymerization is carried out in water at room temperature. The initiator used is the redox pair ammonium persulphate $((NH_4)_2S_2O_8)$ (20 g/l)—sodium metabisulphite $(Na_2S_2O_5)$. All the copolymers thus prepared are purified by precipitation from acetone, with the exception of the copolymer T7 whose soluble segments consist of dimethylacrylamide DMAM, which is purified by ultrafiltration and freeze-drying.

The various polymers synthesized are listed in Table 2 below, which presents the quantities of reagents used (indicated in parenthesis).

In the table:
the viscosities are expressed in centipoises (TO BE EXPRESSED IN SI), for a polymer in solution at 5 g/100 ml in water and at a shear rate of $10s^{-1}$, using a cone-plate viscometer at a uniform Brookfield LDV III shear rate;

they were measured in 0.5 M aqueous $LiNO_3$ solution at 20° C. using 4 Shodex OH Pack B803 to B806 columns of 25 cm in series, with refractometric detection. They are expressed in $10^6$ g/mole. The values in brackets are the values in "POE equivalent" (obtained by comparing with polyoxyethylene standards), with refractometric detection.

The copolymer T10 as well as other copolymers of the same family not described here were also analyzed in terms of molecular mass using multiangle laser light scattering detection ("MiniDawn Wyatt), which makes it possible to obtain the absolute molecular mass. By comparing with the masses, as "POE equivalent", of the same polymers, it was evaluated that, for all the polymers presented in Table 2, the absolute molecular mass is of the order of twice the mass as POE equivalent: this estimated value is given in bold characters in the table.

Knowing the average molecular mass of the copolymers, that of the segments with LCST or macromonomers, and the fraction by mass of segments with LCST incorporated into the copolymer, the average number of segments with LCST per polymer (average values by mass), noted Ns in Table 2, can be easily deduced by means of the formula:

$$Ns = fMw(\text{copolymer})/Mw(\text{macromonomer})$$

The values in bold represent the fraction f of segments with LCST in the final copolymer (fraction by mass).

All the copolymers described in Table 2 exhibit a thermoviscosifying character.

TABLE 2

| Co-polymer | Monomer | Macromonomer | $Na_2S_2O_5$ | Preparation temperature | Viscosity at 25° C. | Viscosity at 60° C. | Mw | Mw/Mn | Ns |
|---|---|---|---|---|---|---|---|---|---|
| T7 | DMAM (2.8 g) | PNIPAM-10 (0.7 g) | 5 g/l | 29° C. | 500 | 8000 | ND | ND | ND |
| T10 | AM (2.8 g) | PNIPAM-10 (0.4 g) 0.065 | 5 g/l | 29° C. | 1000 | 11000 | (1.48) 3 | 4 | 10 |
| T10AA | AM (2.8 g) | (0) 0 | 5 g/l | 29° C. | 800 | 700 | (0.93) 2 | 2.4 | 0 |
| T11 | AM (2.8 g) | PNIPAM-10 (0.8 g) 0.12 | 20 g/l | 23° C. | 100 | 1000 | (0.38) 0.75 | 3.6 | 4 |
| T12 | AM (2.8 g) | PNIPAM-5 (0.8 g) 0.12 | 20 g/l | 23° C. | 30 | 2000 | (0.37) 0.75 | 4.8 | 7 |
| T13 | AM (2.8 g) | PNIPAM-5 (0.8 g) 0.12 | 10 g/l | 23° C. | 100 | 10000 | ND | ND | ND |
| T15 | AM (2.8 g) | PNIPAM-5 (0.4 g) 0.065 | 5 g/l | 25° C. | 200 | 13000 | ND | ND | ND |
| T16 | AM (2.8 g) | PNIPAM-5 (0.4 g) 0.065 | 5 g/l | 29° C. | 800 | 15000 | (1.1) 2.2 | 2.2 | 11 |
| T21 | AM (2.8 g) | PNIPAM-20 (0.8 g) 0.12 | 20 g/l | 23° C. | 30 | 1800 | ND | ND | ND |
| T22 | AM (2.8 g) | PNIPAM-20 (0.4 g) 0.065 | 5 g/l | 23° C. | ND | ND | (1.0) 2 | 5 | 4 |
| T24 | AM (2.8 g) | PNIPAM-M (0.4 g) 0.065 | 5 g/l | 29° C. | ND | ND | (1.4) 3 | 6.6 | 12 |

TABLE 2-continued

| Co-polymer | Monomer | Macromonomer | $Na_2S_2O_5$ | Preparation temperature | Viscosity at 25° C. | Viscosity at 60° C. | Mw | Mw/Mn | Ns |
|---|---|---|---|---|---|---|---|---|---|
| T25 | AM (2.8 g) | PNIPAM-C (0.4 g) 0.065 | 5 g/l | 29° C. | ND | ND | (1.1) 2.2 | 4.9 | 13 |
| T26 | AM (2.8 g) | PNIPAM-L (0.4 g) 0.065 | 5 g/l | 24° C. | ND | ND | (1.5) 3 | 4.7 | 8 |

The procedure presented below is given for the preparation of the copolymer T7. The procedures for the other copolymers may be deduced therefrom by modifying the nature and the concentration of the reagents, and optionally the reaction temperature in accordance with Table 2.

PNIPAM-10 and the monomer considered as well as 30 ml of distilled water are introduced into a 100 ml round-bottomed flask. This mixture is stirred for two hours at room temperature with bubbling of nitrogen so as to remove the dissolved dioxygen.

The mixture is then heated to the temperature chosen for the polymerization using a thermostated bath and the initiators are then added in the form of a solution of $(NH_4)_2SO_8$ at 20 g/l and a solution of $Na_2S_2O_5$ at 5 g/l, that is 0.1% and 0.03% by mole, respectively, of the quantity of monomers introduced. The stirring and the bubbling are maintained for 4 hours.

Before introducing the initiators, and then every hour during the polymerization, samples of the reaction medium are collected (0.1 ml diluted in 5 ml of methanol) in order to monitor the variation of the reaction by steric exclusion chromatography.

Generally, the data associated with the visual observation of the increase in the viscosity of the reaction medium make it possible to conclude the good progress of the reaction, with a practically total yield.

b) Purification

The purification of the polymers is carried out differently depending on the nature of the skeleton.

For polymers whose skeleton consists of DMAM, ultrafiltration was used according to the following procedure:

The reaction medium is diluted in one liter of water and then ultrafiltred on a membrane whose cut-off is 100000 Daltons. The solution of polymer is then concentrated and then freeze-dried.

The yield is quite variable, generally around 60%.

The macromolecules with an acrylamide skeleton are precipitated from acetone according to the following an procedure:

The reaction medium is slowly precipitated from 1 liter of acetone and then filtered on No. 4 sintered glass and washed with three times 100 ml of acetone. The solid is recovered and then dried overnight using a slide vane rotary vacuum pump.

The mass yield is much higher than for ultrafiltration-freeze-drying and is close to 90%.

The level of incorporation of the macromolecules was checked by proton NMR on the polymers diluted to 2 g/100 ml in heavy water (Bruker apparatus at 250 and 400 MHz). It is found that the incorporation level depends only, except for experimental fluctuations, on the ratio between the initial mass of PNIPAM and the initial mass of hydrophilic monomer. It is 6.5+/−0.3% by mole, for an initial concentration of 0.4 g of PNIPAM per 2.8 g of acrylamide, and 12+/−1% by mole, for an initial concentration of 0.8 g of PNIPAM per 2.8 g of acrylamide, respectively.

EXAMPLE 3

Evaluation of the rheological behaviour of DMAM/PNIPAM and AM/PNIPAM copolymers prepared according to Example 2 as a function of the temperature.

In this example, each of the copolymers was introduced in an amount of 5 g/100 ml into purified water (MilliQ). The viscosity of each of the corresponding solutions was measured on a Brookfield DV3 cone-plate rheometer controlled by the Rheocalc software (Sodexim, Muizon, F). The shear rate selected is 10 (1/s) for a temperature gradient of 1° C. per minute. The results obtained are represented in FIG. 1.

It can be observed that the various copolymers synthesized indeed exhibit the rheological properties which make it possible to use them according to the invention, and in particular, that they exhibit a viscosity V2 at a temperature T2 which is significantly higher, by a factor greater than 2 (100%), often of the order of 10, and which may be up to a factor of 60, than the viscosity V1 obtained at a temperature T1 which is less than T2 by at least 20°.

For the polymers described in this example, the temperature T1 may be between 20 and 40° C., or even less, and the temperature T2 may be greater than 45°, and preferably of the order of 60° C.

It is also observed that the polymer T10AA, prepared as a control according to the same protocol but without PNIPAM macromonomer, and which cannot therefore have in its structure the multiplicity of blocks with LCST which characterizes the copolymers according to the invention, exhibits a viscosity which decreases weakly and continuously as a function of the temperature, and cannot therefore exert the beneficial effects of the invention.

Moreover, for all the copolymers and at a rate of change in temperature of 1° C. per min, no significant hysteresis is observed, the viscosity curve being essentially identical when the temperature rises or decreases.

By comparing FIG. 1 and Table 2, it is noted that the viscosity at low temperature is highly correlated with the molecular mass of the copolymer. It is also observed that the thermoviscosifying behaviour and the increase in viscosity with temperature are highly correlated with the average number of segments with LCST per chain Ns, the highest values for this parameter corresponding to the highest thermoviscosifying effects.

FIG. 2a illustrates the rheological behaviour of the copolymer T10 in an ionic electrolyte such as for example potassium carbonate, or alternatively a buffer of the TRIS-TAPS 50 mM/Urea 7M type as used for the sequencing.

In FIG. 2b, there are represented the behaviours of two solutions based on the copolymer PAM-NIPAM T10, one for a concentration of 3 g/100 ml of copolymer and the other for a concentration of 2 g/100 ml of copolymer. It is noted that the thermothickening character is sensitive from 2 g/100 ml, but is reinforced at 3 g/100 ml and even more at 5 g/100 ml (FIG. 1), the concentration also being a parameter which will be varied in a useful manner in order to adapt the media according to the invention according to the particular applications.

In particular, most of the polymers presented in Table 2 exhibit, for concentrations of less than or equal to 5 g/100 ml, a thermoviscosifying character, that is to say that they do not exhibit significant hysteresis of their viscosity as the temperature rises and decreases, and are capable of flowing in less than 30 s when the vessel is turned over.

The polymer T16, on the other hand, gives rise to a gel-type state at 60° C. for concentrations of 8 g/100 ml and more.

EXAMPLES 4

Properties of separation of separation media for capillary electrophoresis comprising, as copolymer, one of the copolymers prepared according to Example 2.

The electrophoresis experiments presented in this example and in the following examples were carried out using a laboratory-constructed apparatus similar to that described in Lindberg et al., Electrophoresis, 18, 1973 (1997). The DNAs separated are detected by fluorescence with excitation by an Argon laser at 488 nm and emission at 530+/−30 nm. The injection is of the electrokinetic type. The capillary, made from molten silica coated with polyimide (polymicro), having a diameter of less than 100 µm, is thermostated between the point of injection and the point of detection by circulation of silicone oil in a sealed envelope, with the exception of the first 2 and last 2 centimeters (unless otherwise stated, this type of capillary will be used in the electrophoresis experiments presented below).

Trial 4-1

Separating properties of a medium comprising, as copolymer, the copolymer PAM-NIPAM (T15) at a concentration of 2 g/100 ml.

The medium is mixed with TRIS-TAPS buffer (50 mM) and DNA marker (for SYBR GREEN I $10^{-4}$).

In this particular case, the filling of the capillary is carried out at 25° C., the injection is carried out over 10 seconds at 25 volts per centimeter and the sample to be separated is of the same nature as that of the preceding trial.

The separating properties of the said medium are evaluated at two temperatures, 25° C. and 60° C., and FIGS. 3a and 3b present these properties. It is observed that the separation has a higher resolution and is more rapid at 60° C.

Trial 4-2

Separating properties of a separation medium based on the copolymer PAM-NIPAM (T12).

The medium is introduced into the capillary at 25° C. at a concentration of 8 g/100 ml, mixed with TRIS-TAPS buffer (50 mM) and with the DNA marker SYBR GREEN I (molecular probes) diluted at the rate of $10^{-4}$ relative to the stock solution sold by the supplier. A similar behaviour is noted with an improvement in resolution and in separating time when the temperature chosen for the separation is 60° C.

It is also observed that the resolution for large duplex DNA fragments is better with the copolymer T15, prepared with a low level of transfer agent and therefore exhibiting a high molecular mass, than with the copolymer T12 prepared with a higher level of transfer agent and exhibiting a lower molecular mass.

Trial 4-3

Separating properties of a medium comprising, as copolymer, the copolymer PD MAM-NIPAM (T7) at a concentration of 2 g/100 ml.

This medium is mixed with the TRIS-acetate buffer (50 mM) and with the DNA marker SYBR GREEN I $10^{-4}$.

In this particular case, the sample is the marker "Phi-X 174-RF DNA, Hae III digest" (Pharmacia biotech), whose fragments have sizes of between 72 and 1358 bp, the injection is carried out over 5 seconds at 20 volts per centimeter and the sample to be separated is of the same nature as that in the preceding trial.

The separating properties of the said medium are evaluated at two temperatures, 25° C. and 50° C., and FIGS. 4a and 4b present these properties. It is observed, as in the preceding trial, that the separation has a higher resolution and is more rapid at a higher temperature.

Trial 4-4

Separating properties of a medium comprising, as copolymer, the copolymer PAM-NIPAM T21, prepared from the macromonomer PNIPAM-20, at a concentration of 2 g/100 ml.

The medium is mixed with the TRIS-acetate buffer (50 mM). For this separation medium, the viscosity at high temperature is relatively low, and does not allow total suppression of electroosmosis. Consequently, the capillary was, prior to its use, washed with a 1M hydrochloric acid solution comprising 1 g/100 ml of polyvinylpyrrolidone, having a molecular mass of 1000000 (Polysciences, Eppelheim, D).

In this particular case, the sample is the marker "100 bp fluorescein ladder", Bio-Rad, whose fragments have sizes of between 100 and 1000 bp, the injection is carried out over 10 seconds at 25 volts per centimeter.

The separating properties of the said medium, introduced into the capillary at 25° C., are evaluated at two temperatures, 25° C. and 50° C., and FIGS. 5a and 5b present these properties.

It is observed, as in the preceding trial, that the separation is more rapid at a higher temperature, but that the gain in resolution is lower than with for example T15 or T7, which exhibit a more marked thermothickening character. This confirms that the thermothickening character, as it appears in the viscosity curves as a function of the temperature, is a characteristic advantage of the media according to the invention, and that the said viscosity curves may be used as a guide for optimizing the separation properties.

Trial 4-5

Separation of the sequence products using a separation medium comprising the copolymer PAM-NIPAM (T10).

The copolymer is used at two different concentrations, 3 g/100 ml and 5 g/100 ml, respectively, in TRIS-TAPS buffer (50 mM) containing 7M urea. The pH of the medium is of the order of 8.2. As a control, a trial is carried out with a commercial sequencing medium (POP6 Perkin-Elmer), used as received.

The capillary used has a length of 40 cm, with an effective length of 30 cm and an internal diameter of 100 µm. For the separation media based on T10 polymer, which do not exhibit specific properties of adsorption on silica, the capillary is, prior to its use, washed with a 1M hydrochloric acid solution and comprising 1 g/100 ml of polyvinylpyrrolidone, having a molecular mass of 1000000. The separation medium is introduced into the capillary at 25° C.

The sample tested is the product of a reaction of sequence of DNA ssM13mp18, (fragments with "T" ending), prepared by cyclic sequencing with the fluorescein-primer kit distributed by Amersham, according to the instructions provided by the manufacturer.

The electric field is 200 volts per centimeter and the injection is carried out over 8 seconds at 200 volts per centimeter. The separating capacities of each of these media are evaluated at the temperature of 60° C. FIGS. 6 and 7 present the separating capacities of the commercial sequencing medium (control Figure a), and the media according to the invention based on the copolymer T10 at the respective concentrations of 3 g/100 ml (Figures b) and 5 g/100 ml (Figures c) (the numbers above the peaks represent the length of the DNA fragment minus 48 bases).

Trial 4-6

Separating properties with respect to fragments of sequences using various separation media in accordance with the invention.

The media tested are based either on the copolymer PAM-NIPAM (T12) at a concentration of 8 g/100 ml, on the copolymer PAM-NIPAM (T13) with a concentration of 5 g/100 ml or on the copolymer DMAM-NIPAM (T7) with a concentration at 5 g/100 ml, respectively.

Each of these media is of course supplemented with TRIS-TAPS buffer (50 mM) and with 7M urea. They have a pH of 8.2, the nature of the sample and the separation conditions are the same as those chosen in the context of the preceding trial.

These different trials confirm that several media according to the invention, having a relatively moderate viscosity at room temperature of the order of 1000 mPa.m$^{-1}$.s$^{-1}$, or even markedly lower, make it possible to separate the DNA sequence fragments with performances equal to or greater than those of the commercial media. It will be observed in particular that the resolution obtained with T10 at 5 g/100 ml is markedly greater than that obtained with POP6, in a slightly shorter time.

Trial 4-7

Separation using DNA fragments of a medium comprising, as copolymer, the copolymer PAM-NIPAM (T10).

The copolymer used at a concentration of 2 g/100 ml is mixed with the TRIS-TAPS buffer (50 mM), 2 mM EDTA and with the DNA marker SYBR GREEN I 10$^{-4}$. The length of the capillary is 15 cm, of which 10 cm up to the detector, and the capillary is of the "DB17" type (JW scientific) having an internal diameter of 100 micrometers, so as to eliminate the residual electroosmosis which appears with this medium.

In this particular case, the sample is the marker High molecular weight standard (Life Technologies), and has fragments between 8 271 and 48 502 base pairs. The injection is carried out over 5 seconds at 100 volts per centimeter. The separation is carried out in a pulsed field with square pulses of +/−200 V, an asymmetry between the + and − pulses of 20% and a frequency of 30 Hz. The separation of the fragments may be carried out in less than 20 min (FIG. 8), against several hours in an ordinary entangled polymer solution (Heller et al. Electrophoresis, 16, 1423–1428 (1995)).

Trial 4-8

Separation and resolution properties at 40° C. of separation media in accordance with the invention.

The media tested contain polymers based on NIPAM macromonomers of different length (T22, T26, T24 and T25, respectively), dissolved at 3 g/100 ml in TRIS-TAPS buffer (50 mM) containing 7M urea. The pH of the medium is of the order of 8.2. The sample used is "50 BL LADDER-fluorescein", Pharmacia.

The results, in terms of peak width, are given in FIG. 12.

It is evident therefrom that the best resolution (lower peak width) is for that series obtained with the polymer T24 (prepared from macromonomers having an average molecular mass of 15000), and that the media based on T25 and T26 also give very satisfactory results sufficient to carry out good quality sequencing.

Trial 4-9

Separation of reaction products of sequence using a separation medium according to the invention at constant temperature.

The medium tested is of the T16 type, at 5 g/100 ml, in 50 mM Na TAPS buffer containing 2 mM EDTA and 7M urea, the said medium being introduced into the capillary at 50° C., and the separation also being carried out at 50° C. An ABI 310 apparatus is used.

It is noted that the reading can be carried out very well up to more than 500 bases, and that the introduction at low temperature is not, in this precise case, essential to using the medium according to the invention. This advantageous property results from the fact that the medium is of the thermoviscosifying type and does not therefore exhibit, at the temperature at which the separation is carried out, a gel-type state which would prevent its introduction into the capillary.

EXAMPLE 5

Preparation of PVA-NIPAM (Polyvinyl Alcohol/Poly-N-Isopropylacrylamide) copolymers.

The polyvinyl alcohol constituting the water-soluble skeleton of the copolymer is obtained beforehand by hydrolysing polyvinyl acetate. The polymer used for the study has an acetate level of 12.4 mol% and a weight-average molar mass of 145000 g/mol. Its intrinsic viscosity in water at 30° C. is 92 ml/g, the critical concentration for covering the C* chains is about 1.25 g/100 ml.

The route of synthesis followed is of the "grafting from" type. It is described by Nonaka et al. in homogeneous medium (Y. Nonaka, Y. Ogata, S. Kurihara, Journal of Applied Polymer Science, vol. 52, 951–957 (1994)) or Ikada et al. in the case of a poly(methyl methacrylate) skeleton (Y. Ikada, Y. Nischizaki, I. Sakwada, J. Polym. Sci., Vol. 12, 1829–1839 (1974)).

The synthesis is carried out at 60° C. for 20 hours in dimethyl sulphoxide (DMSO), in the presence of potassium persulphate (KPS) in order to generate radicals on the PVA skeletons. These radicals then induce the polymerization of the monomer present in the medium, leading to the final product.

The formation of carbonyl groups according to a secondary reaction of ketoenolic tautomerism causes the appearance of a yellow colour which is effectively observed during the synthesis.

Table 3 below presents the characteristics of the PVA-NIPAM obtained according to this protocol.

TABLE 3

|  | m (g) or V (ml) |
|---|---|
| PVA | 5 g |
| NIPAM | 5 g |
| KPS | 0.08 g |
| DMSO | 100 ml |
| KPS/PVA molar ratio | 0.26 |
| homoNIPAM | |
| m (g) | 0.772 |
| Mw$^b$ (g/mol) | 19 300 |
| Copolymer | |
| m (g) | 8.9 |
| yield (%) | 89 |
| Grafting level$^c$ % weight NIPAM | 32.3 |

[b]determined by SEC in THF at 40° C., with ultrastyragel column (Waters 150 CV+ chromatograph), refractometric detection and single calibration with respect to polystyrene standards.
[c]determined by NMR.

EXAMPLE 6

Preparation of a linear triblock copolymer POP-POE-POP

This copolymer is prepared according to a protocol derived from that described by J. P. Kaczmarski and J. E. Glass, Langmuir, 1994, 10, 3035–3042.

About 10 g of polyethylene glycol having a molecular weight of 35000 (Merck, Hohenbrunn, D) (PEG) and 100 ml of anhydrous toluene are mixed under an argon atmosphere (the low-molecular-weight polyoxyethylenes are commonly called "polyethylene glycol"). Once the PEG is dissolved in the toluene, the mixture is heated under reflux under argon and approximately 10 to 15 ml of anhydrous toluene are evaporated off. The solution is cooled to room temperature and 120 mg (0.2% by weight) of dibutyltin dilaurate are added to the solution. A stoichiometric quantity of isophorone diisocyanate (128 mg) is dissolved in 5 ml of anhydrous toluene and added to the mixture. The reaction is monitored by visualizing using infrared spectroscopy (by enhancing the reduction in the isocyanate band at 2260 $cm^{-1}$). At the end of 90 minutes, 2.4 g of polypropylene glycol monobutyl ether (Mn 400) (PPG) (Aldrich, Milwaukee, USA) are dissolved in 20 ml of anhydrous toluene and added dropwise to the mixture (the low-molecular-weight polyoxypropylenes are commonly called "polypropylene glycol"). The reaction is continued overnight (about 15 hours) at 5° C. (the isocyanate band decreases from the beginning of the reaction and then stabilizes). 80 ml of toluene are added to the mixture in order to reduce the viscosity of the solution and the polymer is precipitated using 550 ml of petroleum ether, filtered on No. 4 sintered glass, washed with excess petroleum ether and dried under vacuum.

EXAMPLE 7

Determination of the thermothickening behaviour of a PVA-NIPAM copolymer and of a linear triblock copolymer POP-POE-POP.

The rheometer-used in this example is identical to that used in Example 3 above. The PVA-NIPAM used corresponds to that in Table 3 and the linear triblock copolymer POP-POE-POP is that prepared in Example 6.

In FIG. 9 are represented the rheological behaviours of media having

Figure 9A:
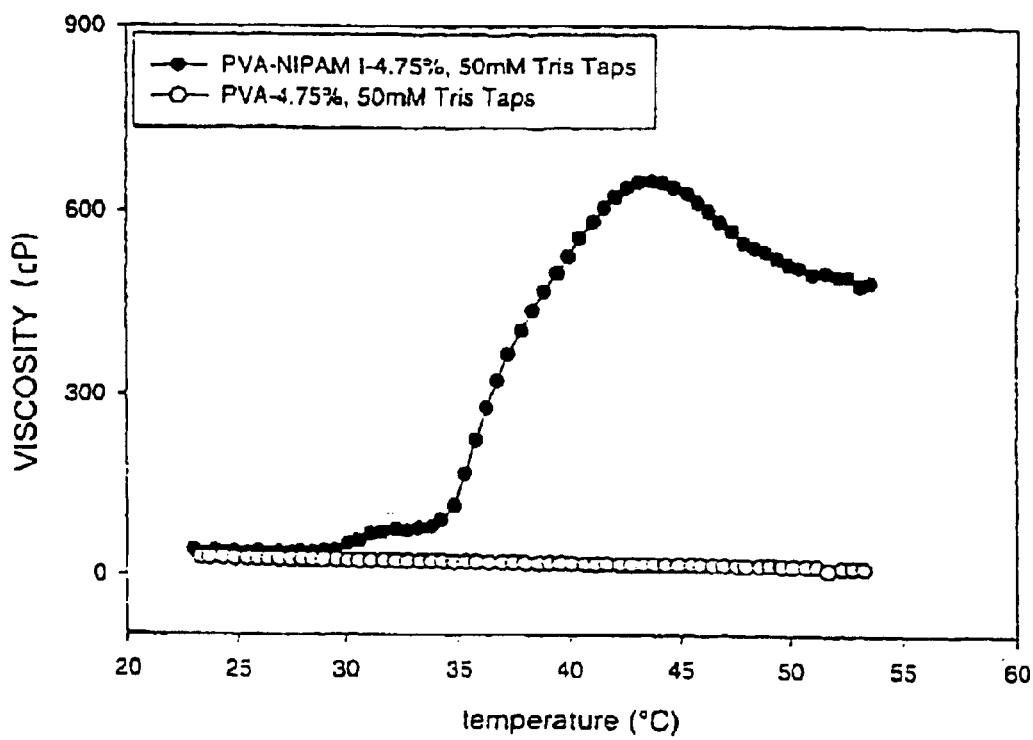
Figure 9B:
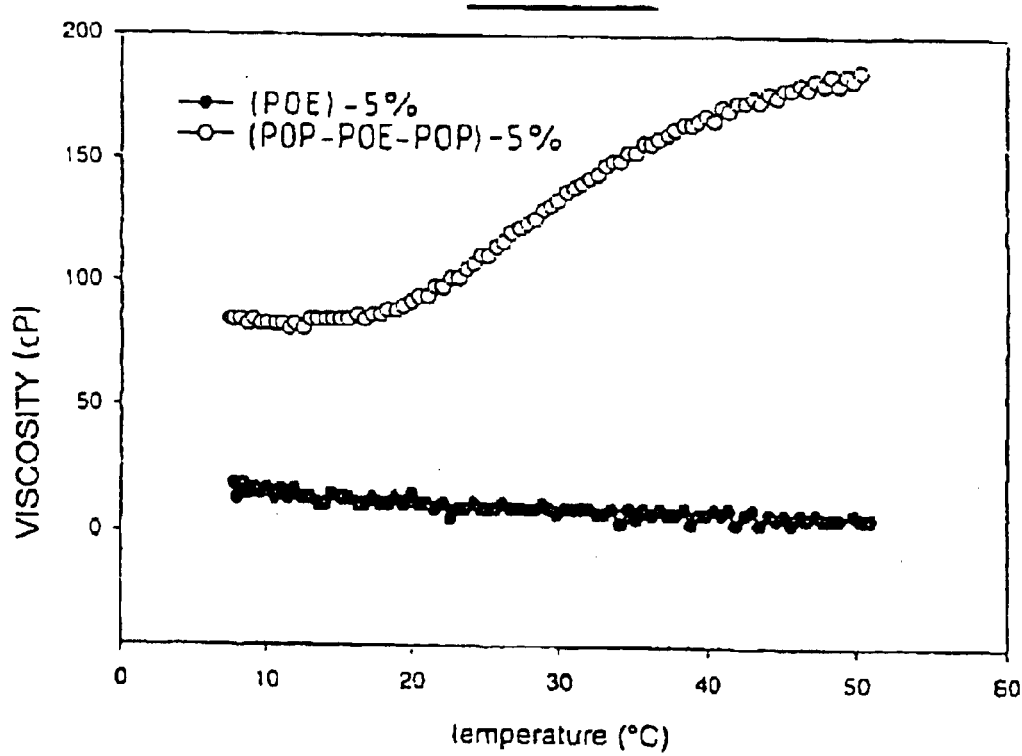

- respectively 4.5% by weight of PVA-NIPAM or 4.75% by weight of PVA dissolved in a 50 mM TRIS-TAPS electrolyte (FIG. 9a). It is observed that the PVA-NIPAM copolymer exhibits a thermothickening character from a temperature greater than 35° C., which PVA alone does not exhibit, and
- the thermocrosslinking character of the linear triblock copolymer POP-POE-POP which thickens rapidly from a temperature of 20° C. (FIG. 9b). Also shown on this graph is the rheological behaviour of the polyethylene glycol polymer at the same concentration. In this case, no increase in viscosity as a function of the temperature is observed.

EXAMPLE 8

Separation properties of an electrophoretic separation medium comprising a PVA-NIPAM copolymer according to Example 5.

The fluorescence detection is performed under the same conditions as those described in Example 4. As regards the capillary channel, it has a total length of 40 cm and an effective length of 30 cm, an internal diameter of 100 $\mu$m and it is coated with an acrylamide derivative according to the process described by HJERTEN J. Chromatogr., 1985, 347, 191 in order to eliminate electroosmosis.

The electrolyte comprises 4.75 g/100 ml of PVA-PNIPAM copolymer and 50 nM of TRIS-TAPS buffer.

The electric field is 200 volts per centimeter. The injection is carried out over 10 seconds at 200 volts per centimeter. The sample is the sizer 50-500, Pharmacia Biotech, diluted 1/500 in MILI Q water (Miliport).

The separating properties are assessed at two temperatures, 20° C. (FIG. 10a) and 44° C. (FIG. 10b). The separating time is improved, but the resolution is not markedly increased, which is undoubtedly due to the excessively low viscosity reached at 44° C. for this medium.

EXAMPLE 9

Separating properties of a separation medium comprising, as copolymer, a triblock copolymer POP-POE-POP according to Example 8.

The medium was tested under the conditions recommended for the medium described in Example 7 above.

The results obtained are represented in FIG. 11.

FIG. 11a presents the separating properties of the control medium, that is to say simply based on unmodified polyethylene glycol, at 20° C. FIG. 11b presents the separating properties of a medium comprising the copolymer POP-POE-POP at a temperature of 20° C. by analogy with the control medium and FIG. 11c illustrates the separating properties of a medium based on the said copolymer but at a temperature of 50° C. This shows that the coopolymer exhibits, from room temperature, a resolution greater than that obtained with POE alone, undoubtedly because of its higher molecular mass, but that the properties are again greatly improved when 50° C. is reached, and shows that the polymers of the block type having at least two blocks with LCST, may also be advantageously used in the context of the invention to carry out electrokinetic separations.

EXAMPLE 10

Preparation of a charged copolymer PAAgNIPAM (Polyacrylic Acid/Poly-N-Isopropylacrylamide).

The polyacrylic acid used is in solution at 12.5 g/100 ml in water. The polymer designated PAA500 has a weight-average molar mass of 500000 g/mol (Fluka).

The PAA500 skeleton is sensitive to the pH; the ionizable carboxyl functional groups have a $pK_0$ in the region of 4.25 pH units.

1) Synthesis of the PAAgNIPAM Copolymer a) Procedure

The route of synthesis followed consists in grafting short chains of NIPAM on a small fraction of carboxylic acid functional groups of a polyacrylic acid skeleton. It can be separated into two stages:

Synthesis of oligoNIPAM, a short chain of PNIPAM (Mw≈2000 g/mol) ending with an amine functional group, by free-radical polymerization of NIPAM monomers in methanol in the presence of the transfer agent AET.HCl (2-aminoethanethiol hydrochloride) and of the initiator AIBN (2,2'-azobisbutyronitrile) at 60° C. for 20 hours (this mode of synthesis constitutes an alternative to that, in aqueous solution, used to prepare the PNIPAM-A polymers in Example 1).

The oligoNIPAM of known length are then grafted onto the PAA500 skeleton reaction between acid and amine functional groups in the presence of a podiimide initiator:

- either in water at 60° C. for 1 hour (initiator EDC 1,2-dichloroethane),
- or in N-methylpyrrolidone (NMP) at 60° C. for 24 hours (initiator DCCI dicyclocarbodiimide).

Table 4 presents the composition of the PAAgNIPAM copolymer obtained by this protocol.

TABLE 4

| | Synthesis of PAAgNIPAM I in water | |
|---|---|---|
| | m (g) or V (ml) | n (mmol) |
| OligoNIPAM | 1.7 g | 0.7 |
| PAA500 | 3 g | |
| Initiator | 0.575 g | 3 |
| Solvent | 250 ml | |
| Copolymer | | |
| m (g) | | 4.58 |
| grafting level[a] | | 18 |

[a] % by weight of NIPAM determined by NMR.

EXAMPLE 11

Rheological behaviour of the PAAgNIPAM I copolymer.

The variation of the viscosity as a function of the temperature was plotted under the same conditions as in Example 6 above apart from the use of a shear gradient 100 $s^{-1}$ and a rate of temperature rise of 2° C. per minute. The thermothickening effect appears at 33° C. for PAAgNIPAM I and extends up to 65° C., only exhibiting one growth phase and the beginning of a plateau over this temperature range. This shows that using the examples and descriptions given above, it is also possible to prepare copolymers having a charged hydrophilic skeleton and a multiplicity of blocks with LCST giving rise to thermocrosslinking and which can be used in the context of the invention.

What is claimed is:

1. A heat-sensitive medium for the separation of species in a separating channel, comprising: an electrolyte in which at least a set of block copolymers is dissolved, said block copolymers being provided in said electrolyte at a sufficient concentration to confer to said medium the ability to reversibly transit from a viscosity state V1, obtained at a temperature T1, to a viscosity state V2 which is at least 100% higher than V1, obtained at a temperature T2 between 40° C. and 80° C., wherein said block copolymers comprise on average, in their structure at least a first polymeric segment which is soluble in the electrolyte at the temperatures T1 and T2, and more than two additional non-contiguous polymeric segments exhibiting an LCST in said electrolyte and having an average number of atoms along their main chain which is greater than 50.

2. The medium according to claim 1, wherein the temperature T1 is between 15° C. and 30° C.

3. The medium according to claim 1, wherein the viscosity V2 is greater than the viscosity V1 by at least a factor equal to 5 at the viscosity V1.

4. The medium according to claim 1, wherein the LCST is at least 10% in mass average of said segments with LCST is between T1 and T2.

5. The medium according to claim 1, wherein all the segments with LCST represent between 2% and 25% of the total average molar mass of the copolymers.

6. The medium according to claim 1, wherein all or some of said polymeric segments with LCST possess along their skeleton an average number of atoms greater than 75, or an average molecular mass greater than 2500 Dalton.

7. The medium according to claim 1, wherein all or some of said block polymers exist in the form of linear block polymers.

8. The medium according to claim 1, wherein said block polymers exist at least partially in the form of comb copolymers comprising a main chain and side chains, whose main chain consists of at least one of said first polymeric segment.

9. The medium according to claim 1, wherein all or some of the copolymers possess an average number of said additional polymeric segments per chain greater than 5.

10. The medium according to claim 1, wherein all or some of the copolymers possess a molecular mass greater than 30000 Dalton or a number of atoms along the main chain greater than 2000.

11. The medium according to claim 1, wherein all or some of the copolymers possess a molecular mass of between 50000 Dalton and 3000000 Dalton or a number of atoms along the main chain of between 2500 and 100000 Dalton.

12. The medium according to claim 1, wherein all or some of the copolymers possess an average number of atoms along a section of first polymeric segment, between two consecutive binding points of said soluble segment with said additional polymeric segments, greater than 210.

13. The medium according to claim 1, wherein all or some of said polymeric segments with LCST are derived from one or more copolymers selected from the group consisting of polyvinyl alkyl ethers, hydroxyalkyl celluloses, homopolymers of ether oxides, random and block copolymers of ether oxides, alkylene homo- and copolymers, and polyacrylic derivatives wherein said polyacrylic, derivatives are derived from the homopolymerization or copolymerization of monomers chosen from acrylic and methacrylic acids, alkylacrylates and methacrylates, N-alkyl-acrylamides or -methacrylamides, N',N-dialkyl-acrylamides or -methacrylamides, aryl-acrylamides or -methacrylamides and alkylaryl-acrylamides or -methacrylamides.

14. The medium according to claim 1, wherein the polymeric segment(s) soluble at the temperatures T1 and T2 consist of at least one polymer selected from the group consisting of polyethers, polyesters, soluble random copolymers and homopolymers of polyoxyalkylene, polysaccharides, polyvinyl alcohol, polyvinylpyrrolidone, polyurethanes, polyamides, polysulphonamides, polysulphoxides, polystyrenesulphonate, substituted or unsubstituted polyacrylamides or polymethacrylamides which are soluble in said electrolyte.

15. The medium according to claim 1, wherein said block copolymer is selected from the group consisting of copolymers of the comb copolymer type whose main chain includes acrylamide, acrylic acid, acryloylaminoethanol or dimethacrylamide and on which there are grafted side segments of the poly(N-alkyl or N,N-dialkyl)acrylamide type, or side segments of the random or block, polyoxyethylene/oxypropylene copolymer or polyoxypropylene type, or side segments of the polyether type, and copolymers of the block copolymer type exhibiting along their main chain an alternation of segments of the polyoxyethylene type and of segments of the polyoxypropylene type, or an alternation of segments of the polyoxyethylene type and of segments of the polyoxybutylene type or an alternation of segments of polyethylene and of segments of the polyether type which are more hydrophobic than polyoxyethylene.

16. The medium according to claim 1, wherein said block copolymer is selected from the group consisting of: polyacrylamide/poly(N-isopropylacrylamide) (PAM-NIPAM), polyvinylalcohol/poly(N-isopropylacrylamide) (PVA-NIPAM), polyoxyethylene/polyoxypropylene, polyacrylamide/oxyethylene-oxypropylene copolymer, polyacrylamide/polyoxypropylene, polyacrylic acid/ polyoxypropylene, polyacrylic acid/oxyethylene-oxypropylene copolymer, polyacrylic acid/poly(N-isopropylacrylamide), and polydimethylacrylamide/poly(N-isopropylacrylamide) (PDMAM-NIPAM).

17. The medium according to claim 1, which transits from a viscosity V1 of between 50 and 1000 mPa.m$^{-1}$.s$^{-1}$ (SI unit) at a temperature T1 of between 15 and 30° C. to a viscosity V2 which is greater than V1 by a factor of between 2 and 50 at a temperature T2 of the order of 40° C. or higher and comprises between 5 g/100 ml and 20 g/100 ml of copolymers possessing an average molecular mass of between 30000 Dalton and 2000000 Dalton or a number of atoms along the main skeleton of between 1000 and 60000, a fraction by mass of segments with LCST of between 2% and 20%, and an average molecular mass of the segments with LCST of between 2000 Dalton and 20000 Dalton or an average number of atoms along a segment with LCST of between 35 and 350.

18. The medium according to claim 1, which transits from a viscosity V1 of between 100 and 10000 mPa.m$^{-1}$.s$^{-1}$ at a temperature T1 of between 15 and 30° C. to a viscosity V2 which is greater than V1 by a factor of between 2 and 100 at a temperature T2 of the order of 40° C. or higher and comprises between 1 g/100 ml and 8 g/100 ml of copolymers possessing an average molecular mass of between 500000 Dalton and 3000000 Dalton or a number of atoms along the main skeleton of between 7000 and 90000, a fraction by mass of segments with LCST of between 2.5% and 15%, and an average molecular mass of segments with LCST of between 4000 Dalton and 30000 Dalton or an average number of atoms along a segment with LCST of between 60 and 600.

19. The medium according to claim 1, which transits from a viscosity V1 of between 100 and 10000 mPa.m$^{-1}$.s$^{-1}$ (SI unit) at a temperature T1 of between 15 and 30° C. to a viscosity V2 which is greater than V1 by a factor of between 2 and 100 at a temperature T2 of the order of 40° C. or higher and comprises between 0.1 g/100 ml and 5 g/100 ml of copolymers possessing an average molecular mass greater than 500000 Dalton or a number of atoms along the main skeleton greater than 7000, a fraction by mass of segments with LCST of between 2% and 15%, and an average molecular mass of the segments with LCST greater than 4000 Dalton or an average number of atoms along a segment with LCST greater than 90.

20. The medium according to claim 1, wherein said copolymer is present in said medium and the copolymer concentration is less than 20 g/100 ml.

21. The medium according to claim 1, further comprising an adjuvant selected from the group consisting of particles, water-soluble polymers, nonthermothickening associative polymers, and surfactants.

22. The medium according to claim 21, wherein said copolymer concentration is between 0.1 g/100 ml and 8 g/100 ml.

23. A method for the separation or analysis of species chosen from molecular or macromolecular species, nucleic acid analogues obtained by chemical synthesis or modification, proteins, polypeptides, glycopeptides and polysaccharides, organic molecules, synthetic macromolecules or particles such as mineral particles, latex, cells or organelles comprising the steps of providing a separation channel filled with heat-sensitive medium for the separation of species in a separating channel, comprising an electrolyte in which at least a set of block copolymers is dissolved, said block copolymers being provided in said electrolyte at a sufficient concentration to confer to said medium the ability to reversibly transit from a viscosity state V1, obtained at a temperature T1, to a viscosity state V2 which is at least 100% higher than V1, obtained at a temperature T2 which is at least 20° C. higher than T1, wherein said block copolymers comprise on average, in their structure at least a first polymeric segment which is soluble in the electrolyte at the temperatures T1 and T2, and more than two additional non-contiguous polymeric segments exhibiting an LCST in said electrolyte and having an average number of atoms along their main chain which is greater than 50; introducing in said separation channel the sample containing said species; and performing separation of said sample by applying a field able to transport at least some of said species inside said medium.

24. The method according to claim 23, further comprising sequencing DNA.

25. The method according to claim 24, wherein said particles are selected from the group consisting of latexes, whole cells, whole chromosomes, and organelles.

26. The method according to claim 23, further comprising involving a medium which transits from a viscosity V1 of between 50 and 1000 mPa.m$^{-1}$.s$^{-1}$ (SI unit) at a temperature T1 of between 15 and 30° C. to a viscosity V2 which is greater than V1 by a factor of between 2 and 50 at a temperature T2 of the order of 40° C. or higher and comprises between 5 g/100 ml and 20 g/100 ml of copolymers possessing an average molecular mass of between 30000 Dalton and 2000000 Dalton or a number of atoms along the main skeleton of between 1000 and 60000, a fraction by mass of segments with LCST of between 2% and 20%, and an average molecular mass of the segments with LCST of between 2000 Dalton and 20000 Dalton or an average number of atoms along a segment with LCST of between 35 and 350, to separate molecules having a molecular mass of less than 50000 Dalton or oligonucleotides comprising less than 100 nucleotides, or native or denatured proteins.

27. The method according to claim 23, further comprising involving medium which transits from a viscosity V1 of between 100 and 10000 mPa.m$^{-1}$.s$^{-1}$ at a temperature T1 of between 15 and 30° C. to a viscosity V2 which is greater than V1 by a factor of between 2 and 100 at a temperature T2 of the order of 40° C. or higher and comprises between 1 g/100 ml and 8 g/100 ml of copolymers possessing an average molecular mass of between 500000 Dalton and 3000000 Dalton or a number of atoms along the main skeleton of between 7000 and 90000, a fraction by mass of segments with LCST of between 2.5% and 15%, and an average molecular mass of segments with LCST of between 4000 Dalton and 30000 Dalton or an average number of atoms along a segment with LCST of between 60 and 600, to separate products of reaction of DNA sequences, DNA duplexes of less than 1000 base pairs, denatured proteins or synthetic or natural polymers having a molecular mass of between 20000 Dalton and 1000000 Dalton.

28. The method according to claim 23, further comprising involving medium which transits from a viscosity V1 of between 100 and 10000 mPa.m$^{-1}$.s$^{-1}$ (SI unit) at a temperature T1of between 15 and 30° C. to a viscosity v2 which is greater than V1 by a factor of between 2 and 100 at a temperature T2 of the order of 40° C. or higher and comprises between 0.1 g/100 ml and 5 g/100 ml of copolymers possessing

- an average molecular mass greater than 500000 Dalton or a number of atoms along the main skeleton greater than 7000,
- a fraction by mass of segments with LCST of between 2% and 15%, and
- an average molecular mass of the segments with LCST greater than 4000 Dalton or an average number of atoms along a segment with LCST greater than 90, to separate DNA duplexes having a size of between 500 bases and several millions of base pairs, or particles.

29. The method according to claim 23, further comprising the following steps:

- introducing this medium into a separating channel of an electrophoresis apparatus in a sufficient quantity to constitute its separation medium, said separating channel being maintained at a temperature close to temperature T1;
- thermostating a significant proportion of the channel at a temperature close to T2, either prior to or following the introduction of a sample;
- introducing a quantity of sample at the inlet of the separating channel;
- carrying out the separation at a temperature of the order of T2 in a thermostated portion of the channel; and
- detecting the migration of the analytes initially contained in the sample.

30. The method according to claim 23, wherein said method takes place in an automated electrophoresis apparatus.

31. The method according to claim 23, wherein said method takes place in a microfluidic system.

32. The method according to claim 23, wherein said macromolecular species is a biological macromolecular species selected from the group consisting of DNA, RNA and nucleotides.

33. A capillary electrophoresis device comprising, one or several capillaries or channels, wherein at least one dimension of said capillaries or channels is smaller than one millimeter, and wherein said capillaries or channels are at least partly filled with a separation medium, wherein said separation medium is a heat-sensitive medium for the separation of species in a separating channel, comprising an electrolyte in which at least a set of block copolymers is dissolved, said block copolymers being provided in said electrolyte at a sufficient concentration to confer to said medium the ability to reversibly transit from a viscosity state V1, obtained at a temperature T1, to a viscosity state V2 which is at least 100% higher than V1, obtained at a temperature T2 which is at least 20° C. higher than T1, wherein said block copolymers comprise on average, in their structure at least a first polymeric segment which is soluble in the electrolyte at the temperatures T1and T2, and more than two additional non-contiguous polymeric segments exhibiting an LCST in said electrolyte and having an average number of atoms along their main chain which is greater than 50.

* * * * *